United States Patent
Kasid et al.

(10) Patent No.: US 6,559,129 B1
(45) Date of Patent: May 6, 2003

(54) CATIONIC LIPOSOMAL DELIVERY SYSTEM AND THERAPEUTIC USE THEREOF

(75) Inventors: Usha Kasid, Rockville, MD (US); Prafulla Gokhale, Oak Hill, VA (US); Chuanbo Zhang, Rockville, MD (US); Anatoly Dritschilo, Bethesda, MD (US); Aquilar Rahman, Long Grove, IL (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/538,241

(22) Filed: Mar. 30, 2000

Related U.S. Application Data

(60) Continuation-in-part of application No. 09/354,109, filed on Jul. 15, 1999, now abandoned, which is a division of application No. 08/957,327, filed on Oct. 24, 1997, now Pat. No. 6,126,965.
(60) Provisional application No. 60/041,192, filed on Mar. 21, 1997.

(51) Int. Cl.$^7$ .......................... A01N 43/04; C12Q 1/68; C12P 19/34; C12N 15/86; C07H 21/04
(52) U.S. Cl. .......................... 514/44; 435/6; 435/91.1; 435/458; 536/23.1; 536/24.5
(58) Field of Search .......................... 435/6, 91.1, 455, 435/458; 514/2, 4, 44; 536/23.1, 24.5

(56) References Cited

U.S. PATENT DOCUMENTS

| | | | | |
|---|---|---|---|---|
| 5,641,662 A | * | 6/1997 | Debs et al. | 435/172.1 |
| 5,696,277 A | * | 12/1997 | Hostetler et al. | 554/49 |
| 6,120,798 A | * | 9/2000 | Allen et al. | 424/450 |

OTHER PUBLICATIONS

Theodore Friedman, Overcoming the Obstacles to Gene Therapy, Scientific American, pp. 96–101 Jun. 1997.*
Ronald G. Crystal, Transfer of Genes to Humans: Early Lessons and Obstacles to Success, Science, vol. 270 pp. 404–410 1995.*
Andrea Branch, A good antisense molecule is hard to find, TIBS 23, pp. 45–50 Feb. 1998.*
Inder M. Verma et al., Gene therapy–promises, problems and prospects, Nature, vol. 389 pp. 239–242 Sep. 1997.*
J. P. Schofield et al., Non–viral approaches to gene therapy, British Medical Bulletin, vol. 51, No. 1, pp. 56–71, 1995.*
S. T. Crooke, Basic Principles of Antisense Therapeutics, pp. 1–45, 1998.*

* cited by examiner

*Primary Examiner*—Andrew Wang
*Assistant Examiner*—Jane Zara
(74) *Attorney, Agent, or Firm*—Robin L. Teskin

(57) ABSTRACT

The invention relates to novel cationic lipid formulations and use thereof for treatment of cancer, especially in combination with radiation.

10 Claims, 21 Drawing Sheets

Figure 1:
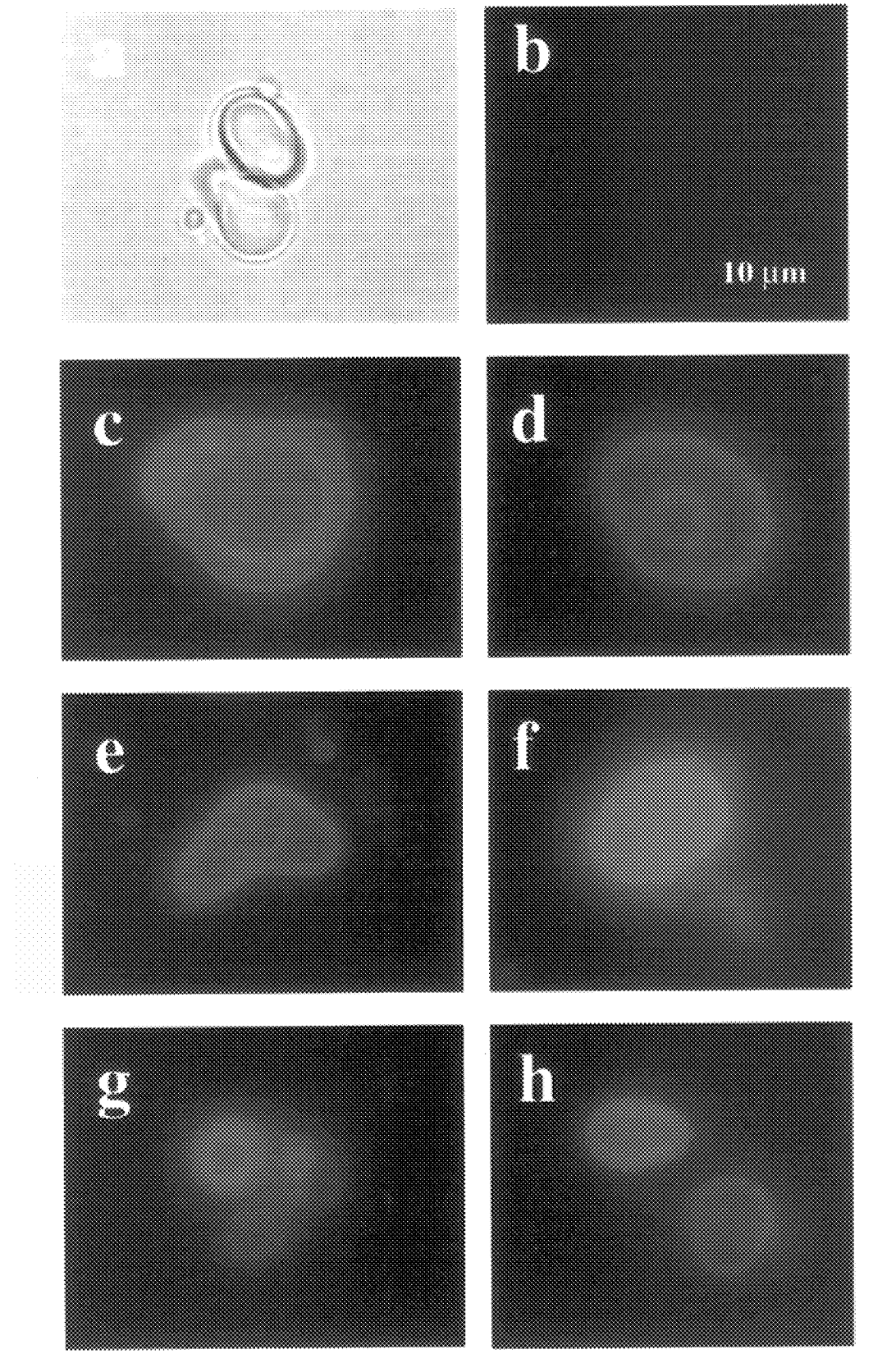

FIG. 2
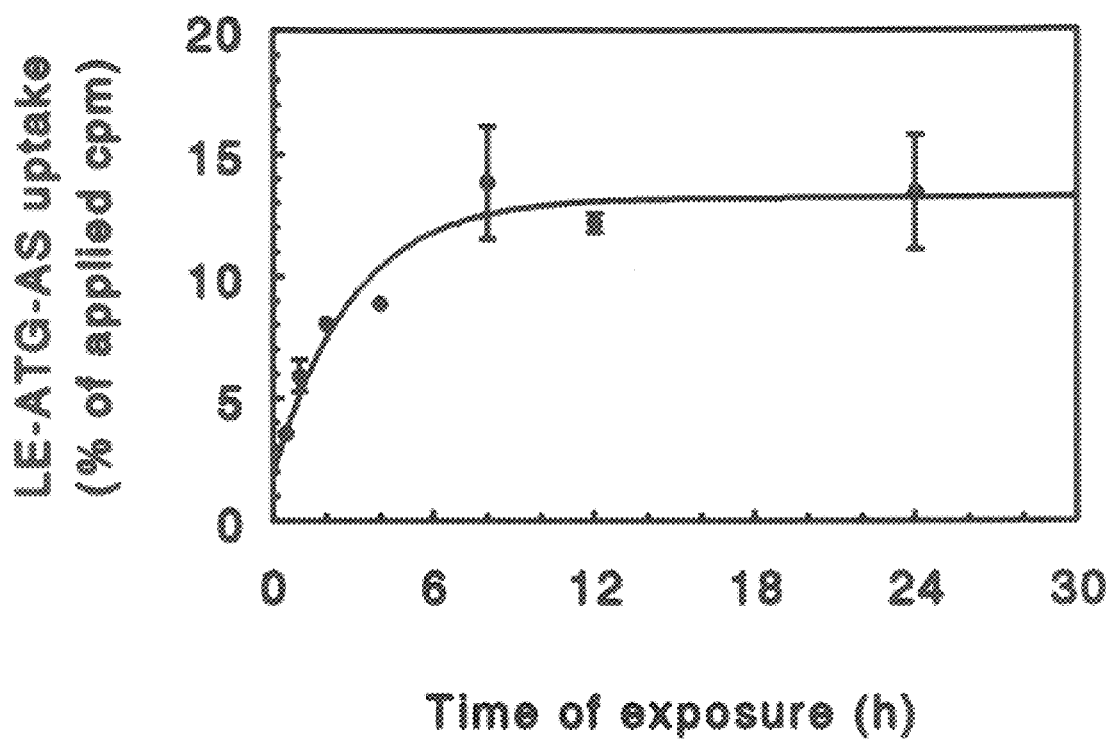
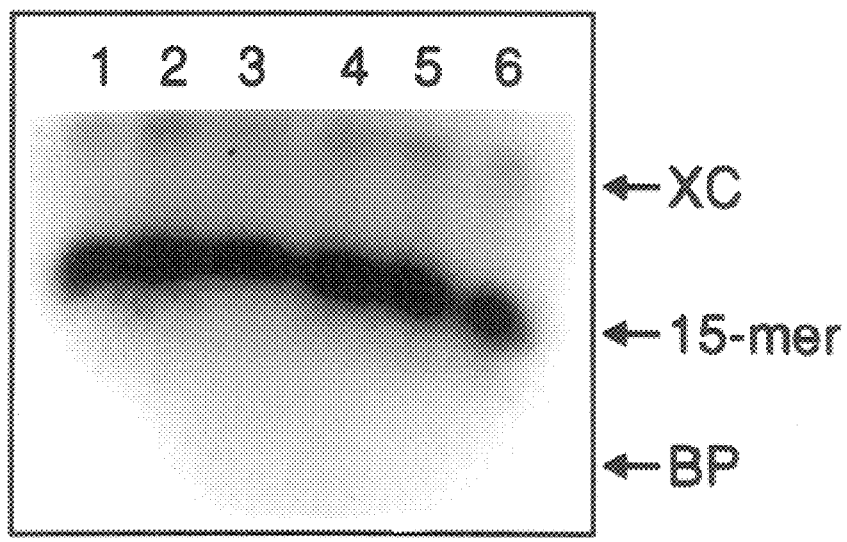

FIG. 3
LE-ATG-AS:
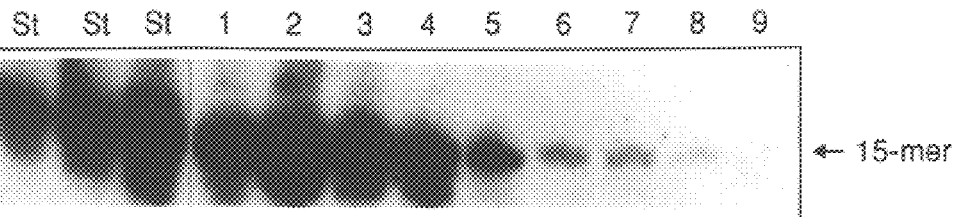
ATG-AS:
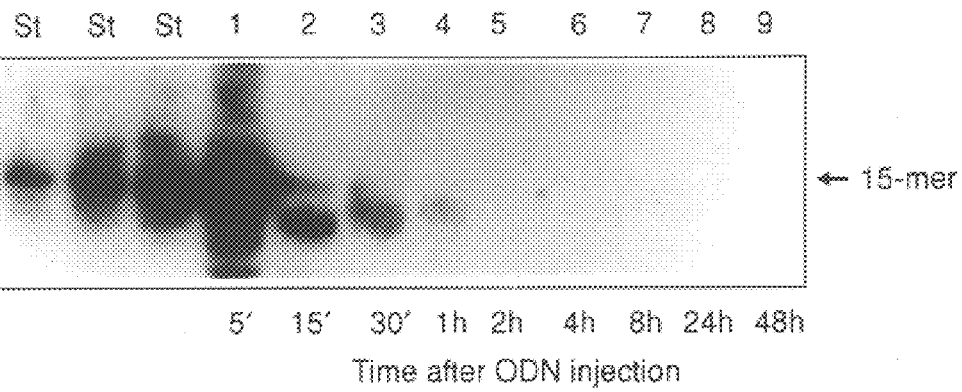
Time after ODN injection
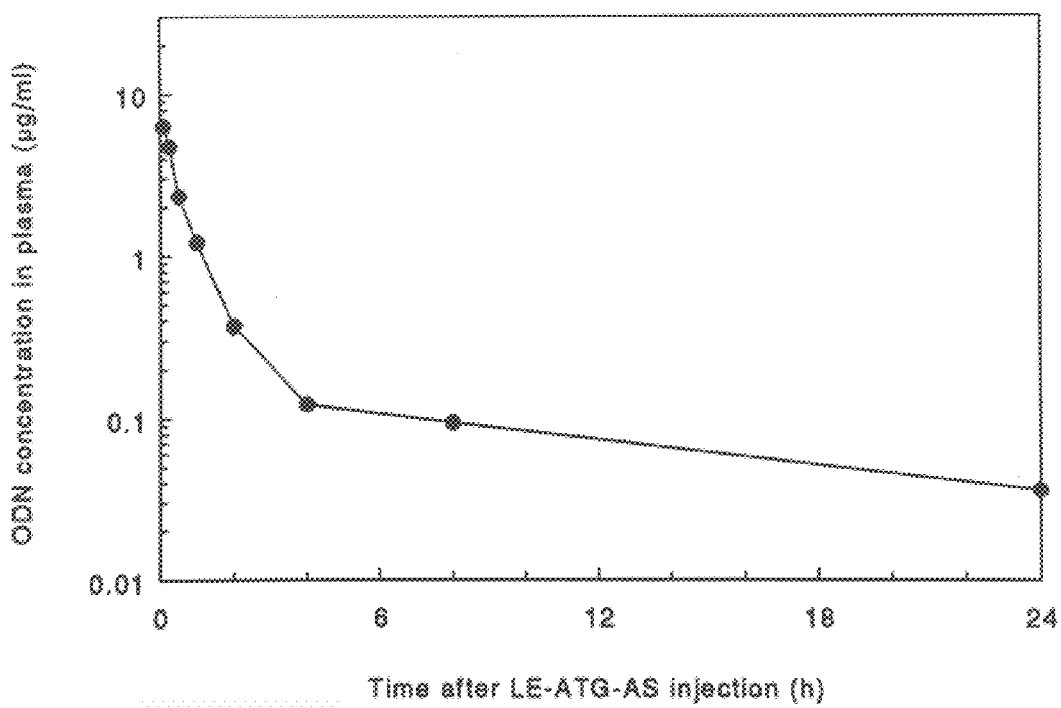
Time after LE-ATG-AS injection (h)

FIG. 4
A
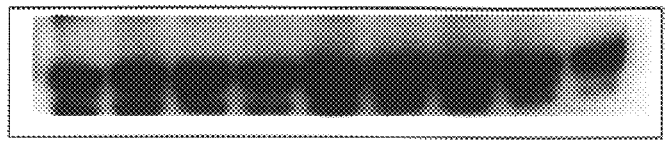
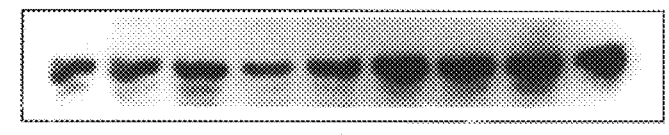
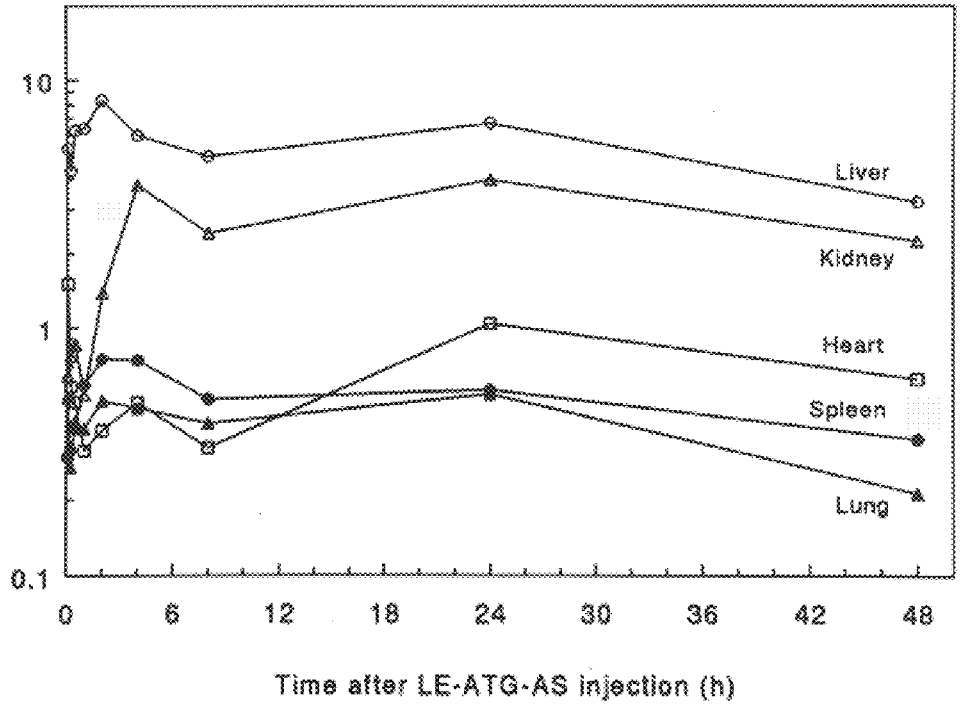

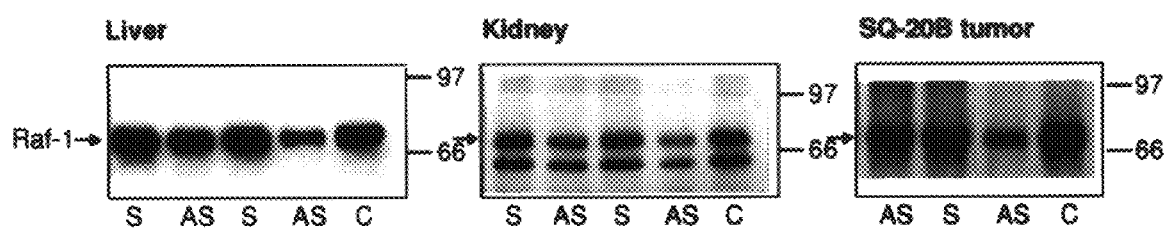
FIG. 7
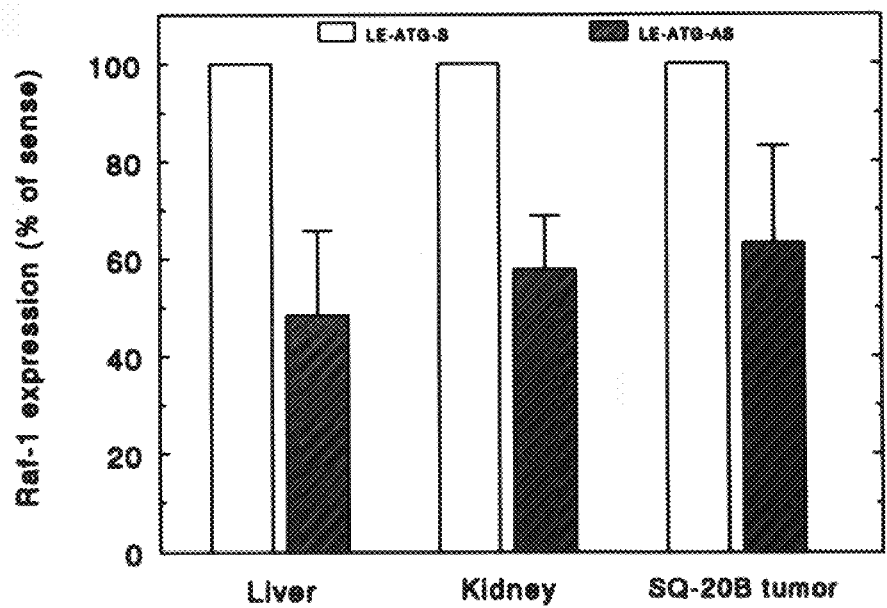

ANTISENSE *ref* AND TUMOR RADIOSENSITIZATION

FIG. 11
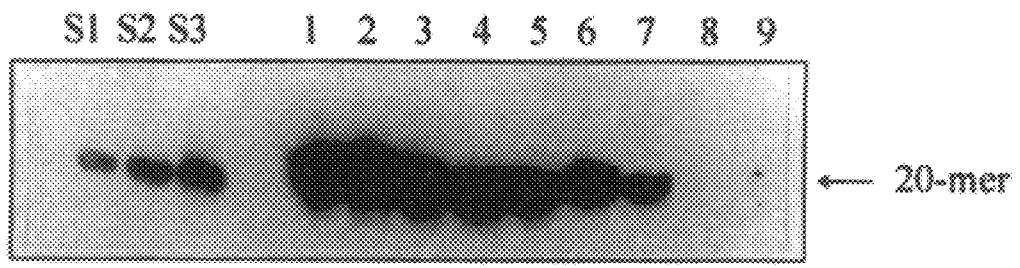
A. LE-5132:
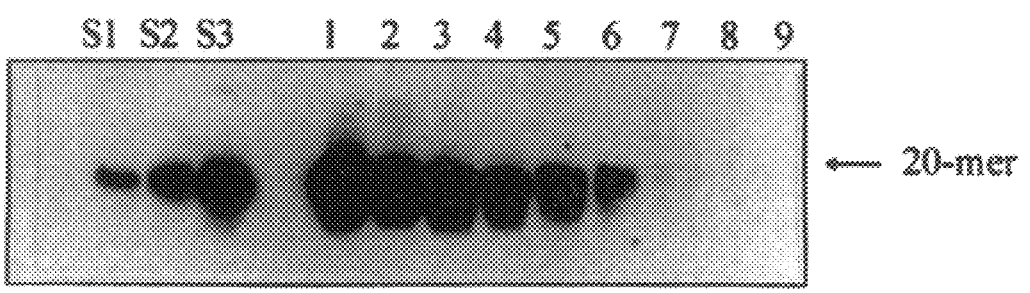
B. ISIS 5132:
5' 15' 30' 1h 2h 4h 8h 24h 48h
Time after ODN injection
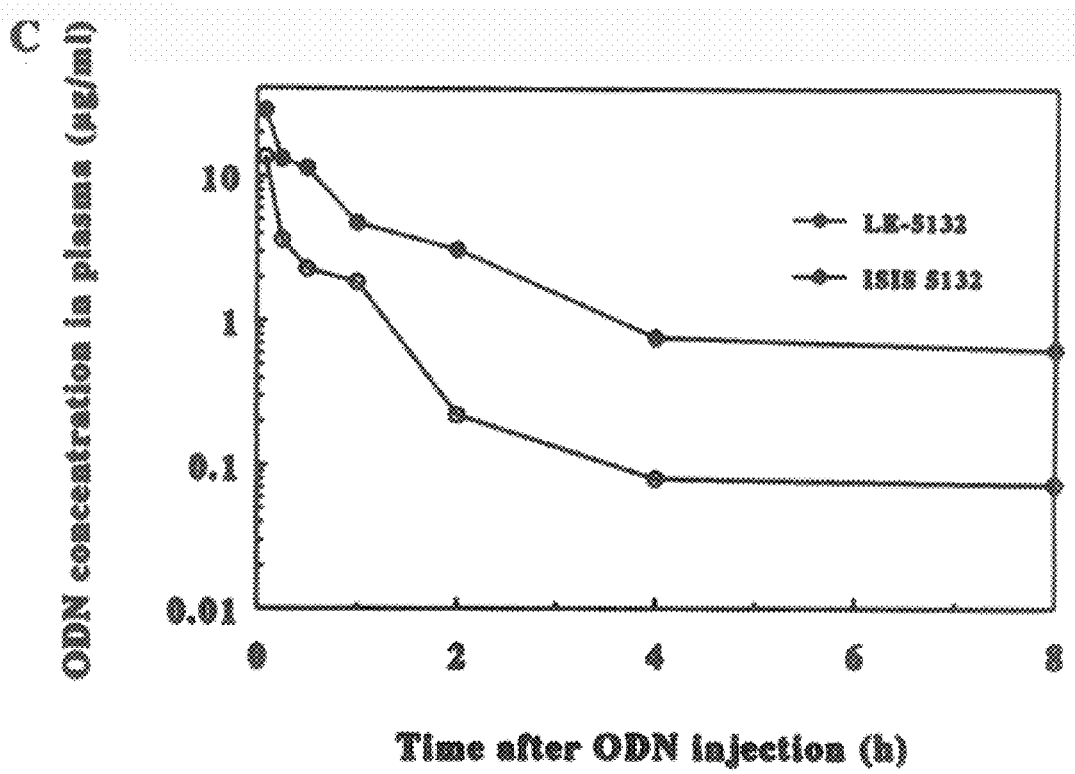
Time after ODN injection (h)

FIG. 15
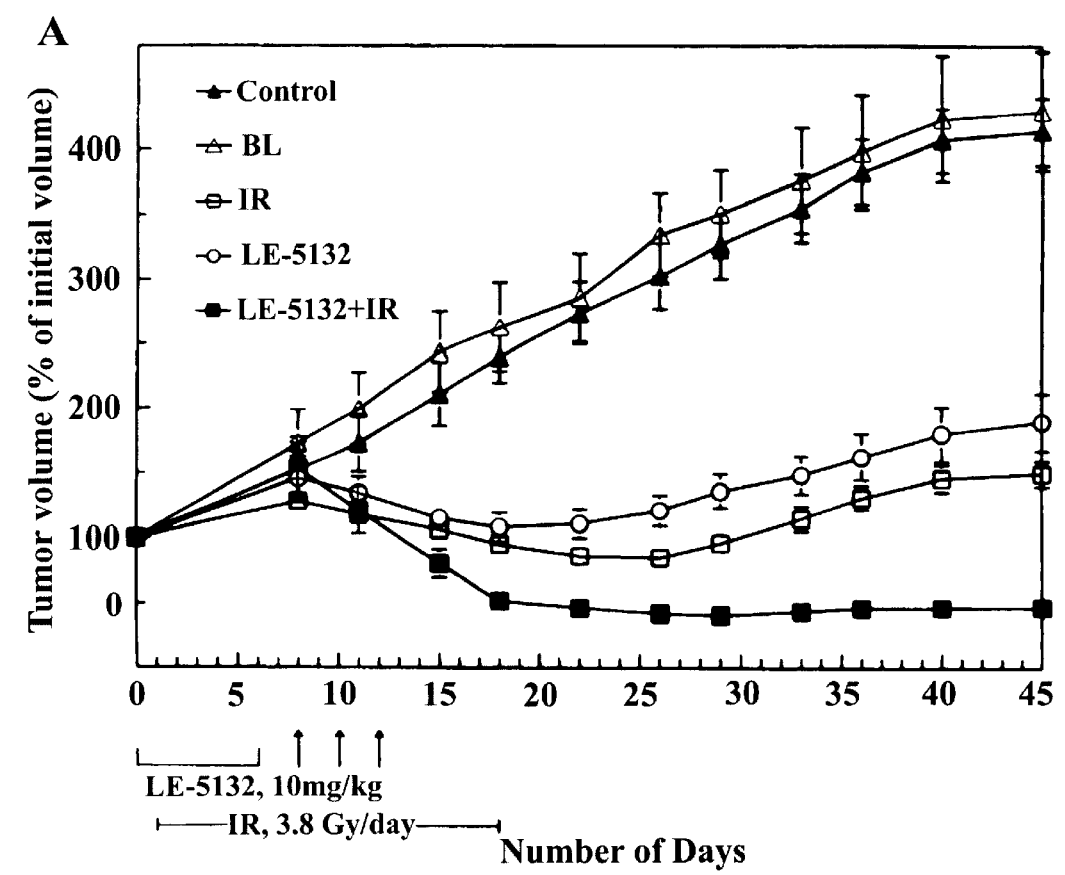
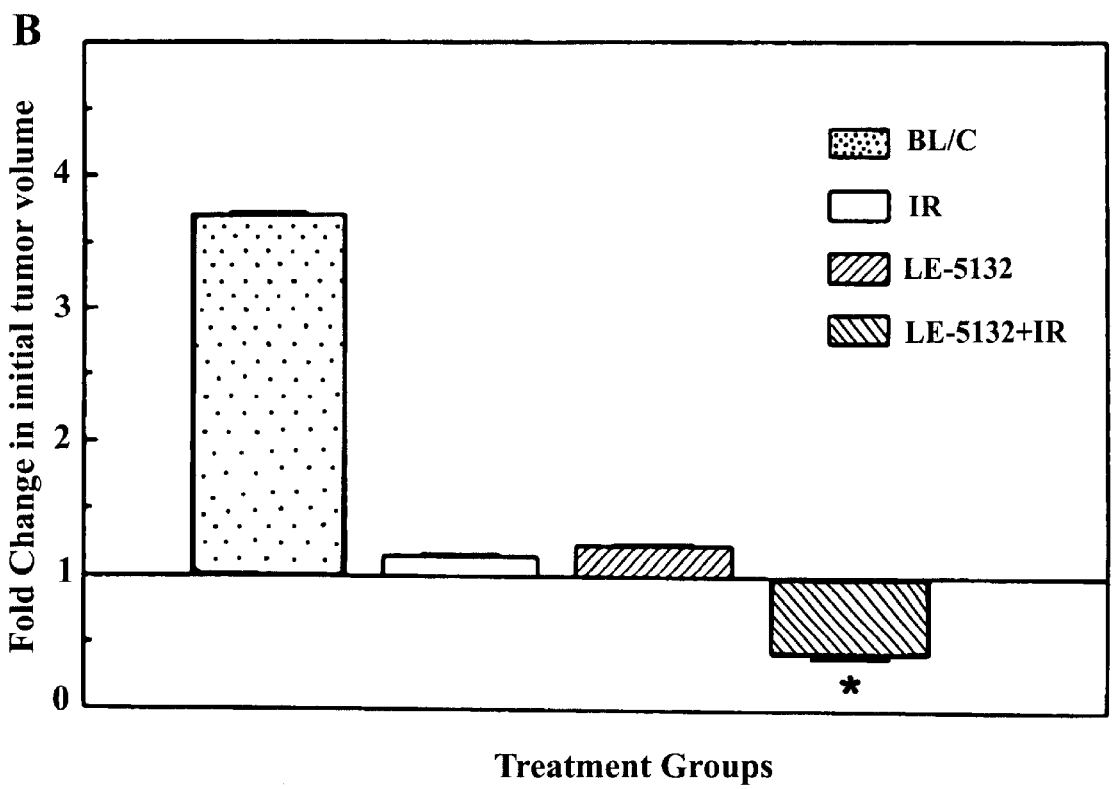

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 15 base pairs
      (B) TYPE: nucleic acid
      (C) STRANDEDNESS: single
      (D) TOPOLOGY: unknown (ii) MOLECULE TYPE: DNA (genomic)

(iii) HYPOTHETICAL: NO (iv) ANTI-SENSE: YES (xi) SEQUENCE DESCRIPTION: SEQ ID NO: 1:

GTGCTCCATT GATGC                                                    15

(2) INFORMATION FOR SEQ ID NO: 2:

```
    (i) SEQUENCE CHARACTERISTICS:
        (A) LENGTH: 25 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: YES (xi) SEQUENCE DESCRIPTION: SEQ ID NO: 2:

CCTGTATGTG CTCCATTGAT GCAGC                                          25

(2) INFORMATION FOR SEQ ID NO: 3:

(i) SEQUENCE CHARACTERISTICS:
        (A) LENGTH: 15 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: YES (xi) SEQUENCE DESCRIPTION: SEQ ID NO: 3:

GCATCAATGG AGCAC                                                     15
```

CATIONIC LIPOSOMAL DELIVERY SYSTEM AND THERAPEUTIC USE THEREOF

RELATED APPLICATIONS

This application is a continuation-in-part of U.S. Ser. No. 09/354,109 now abandoned, filed Jul. 15, 1999, which is in turn a divisional of U.S. Ser. No. 08/957,327, filed Oct. 24, 1997, now U.S. Pat. No. 6,126,965 which claims benefit of priority to Provisional Application Ser. No. 60/041,192, filed Mar. 21, 1997. All of these applications are incorporated by reference in their entirety herein.

GOVERNMENTAL RIGHTS

This work was supported by grants from the National Institutes of Health. The United States Government has certain rights in this invention.

FIELD OF THE INVENTION

This invention is related to novel cationic liposomal formulations for delivery of active agents such as oligonucleotides, proteins, or oligopeptides, oligosaccharides and chemotherapeutic agents. The invention also relates to the use of oligonucleotides, preferably having a size of $\leq 40$ mucleotides for enhancing radiosensitivity of radiation-resistant tumors.

BACKGROUND OF THE INVENTION

Radiation therapy is an important treatment modality of cancer. Such therapeutic methods of therapy include the administration of radiolabeled ligands that bind to a target site, i.e., a tumor, and the irradiation of a tumor using irradiation devices. Radiolabeled ligands used for the treatment of cancer include especially radiolabeled antibodies or radiolabeled peptides that bind to a receptor selectively expressed by a cancer cell.

Recently methods for treating cancers using radiation have improved in the fact that there exist better techniques for selectively targeting radiation to a desired site, i.e., a tumor, thereby minimizing the risk of radiation associated toxicity to normal cells and tissues. However, one prevalent problem with radiation therapy is the fact that many cancers are resistant to the cytotoxic effects of ionizing radiation.

Some researchers have theorized that resistance to irradiation may be linked to certain oncogenes, e.g., ras, raf, cot, mos, myc; growth factors (e.g., PDGF, FGF) and the phenomenon of cellular resistance to ionizing irradiation. For example, it was reported that expression of antisense C-raf-1 cDNA resulted in reduced expression of c-raf-1 gene, and provided for enhanced radiation sensitivity of radioresistant laryngeal squamous carcinoma cells (SE-20B cells) (Kasid et al, *Science*, 243:1354–1356 (1989)).

The use of antisense oligonucleotides for treatment of cancer has also been reported. However, previous problems associated therewith include that such oligonucleotides tend to be unstable in vivo and, therefore, may become degraded before they reach the target site, e.g., tumor cell or viral infected cell.

Attempts to increase the potency of oliogs have included the synthesis of several analogs, with modifications directed primarily to the phosphodiester backbone. For example, phosphorothioate oligonucleotides have demonstrated to exhibit enhanced resistance to nuclease digestion. Other modifications to oligonucleotides have included derivatization with lipophilic moieties such as cholesterol, and polylysine to enhance cellular uptake. Alternatively, the polyanionic nature of the molecule has been eliminated in methylphosphonate analogs.

Another reported approach has involved the use of cationic liposomes to enhance delivery. Bennet et al., *Mol Pharmacol*, 4:1023–1033 (1992).Zelphati et al, *J. Lipsome Res.*, 7(1):31–49 (1997); Thierry et al, *Biochem. Biophys. Res. Comm.*, 190(3):952–960 (1993). It is widely accepted that cationic liposomes must contain enough charge to neutralize the negatively charged oligonucleotides as well as providing enough residual positive charge to the complex to facilitate interaction with a negatively charged cell surface. (Litzinger et al, *J. Liposome Research*, 7(1):51–61 (1997)). However, problems associated with previous cationic liposomal delivery systems similarly include serum-instability, undesirable biodistribution, and target-non-specificity which hinder their use for efficient nucleic acid delivery in vivo.

Thus, improved liposomal delivery systems, especially for delivery of bioactive agents such as oligonucleotides which are stable and result in delivery of an encapsulated active agent to an active site would be highly beneficial. Additionally, improved methods for treating cancers that are radiation-resistant would be beneficial.

OBJECTS AND SUMMARY OF THE INVENTION

It is an object of the invention to provide novel cationic liposomal delivery systems, especially for delivery of oligonucleotides to target cells.

It is a more specific object of the invention to provide cationic liposomes having enhanced serum stability and targeting capability that comprise dimethyldioctadecyl ammonium bromide (DDAB), phosphatidylcholine (PC), and cholesterol (CHOL).

It is another specific object of the invention to provide cationic liposomes that comprise the cationic liposome 1,2-dimyristoyl-3-trimethyl ammonium propane (DMTAP); phosphatidylcholine (PC), and cholesterol (CHOL), and having encapsulated therein a desired active agent, preferably an oligonucleotide.

It is another object of the invention to provide cationic liposomes comprising at least one cationic lipid selected from: 1,2-dioleoyl-3-trimethyl ammonium propane (DOTAP), N-(2,3-(dioleoyloxy)propyl)-N,N,N-trimethyl ammonium chloride, or 1-[2-(9(Z)-octadecenoyloxy)-ethyl]-2-(8(Z)heptadecenyl)-3-(2-hydroxyethyl)-imidazolinium chloride) phosphatidylcholine (PC) and cholesterol (CHOL).

It is an even more specific object of the invention to provide novel cationic liposomes comprising 1,2-dimyristoyl-3-trimethyl ammonium propane (DMTAP); phosphatidylcholine (PC), and cholesterol, wherein the respective molar ratios range from 0.5 to 1.4; 2.0 to 4.0; and 0.5 to 2.5; and more preferably 0.75 to 1.25; 3.0 to 4.0; and 1.25; 3.0 to 4.0; and 1.0 to 2.0; and most preferably about 1:3.2:1.6.

It is another specific object of the invention to provide cationic liposomes comprising dimethyldioctadecyl ammonium bromide (DDAB), phosphatidylcholine (PC) and cholesterol, wherein the respective molar ratios are 0.5 to 1.5; 2.0 to 4.0, and 0.5 to 2.5; more preferably 0.75 to 1.25; 3.0 to 4.0; and 1.0 to 2.0; and most preferably about 1:3.2:1.6.

It is another specific object of the invention to utilize cationic liposomes comprising at least one cationic lipid selected from: 1,2-dimyristoyl-3-trimethyl ammonium propane (DMTAP), dimethyldioctadecyl ammonium bromide (DDAB), 1,2-dioleoyl-3-trimethyl ammonium propane, (DOTAP) N-[2,3-(dioleoyloxy)propyl]-N,N,N-trimethyl ammonium chloride and 1-[2-(9-(Z)-octadecenoyloxy)-ethyl]-2-(8(Z)heptadencenyl)-3-(2-hydroxyethyl)-imidazolium chlorine; phosphatidylcholine and cholesterol, wherein the molar ratio of total cationic lipid, phosphatidylcholine, and cholesterol preferably ranges from 0.5 to 1.5; 2.0 to 4.0; and 0.5 to 2.5; more preferably 0.75 to 1.25; 3.0 to 4.0; and 1.0 to 2.0; and most preferably 0.8 to 1.2; 3.0 to 3.5; and 1.4 to 1.8 as a vehicle for in vivo delivery of active agents, especially oligonucleotides, proteins, peptides, chemotherapeutic agents, growth factors, cytokines, receptors, and antibodies, to a target site, e.g., a tumor or site of an infection. Most preferably, the active agent is an oligonucleotide. This oligonucleotide may be in the sense or antisense orientation relative to a gene target, e.g., an oncogene. Most preferably the oligonucleotide will be an antisense oligonucleotide.

It is an even more specific object of the invention to use the subject cationic liposomes for delivery of active agents, e.g., oligonucleotides, to solid tumors and cancers including head and neck cancer, prostate cancer, pancreatic cancer, breast cancer, lung cancer, kidney cancer, ovarian cancer, brain cancer, esophageal cancer, bladder cancer, liver cancer, colon cancer, penile cancer, B and T cell lymphomas, testicular cancer, bone cancer, and hematologic cancers.

It is another object of the invention to administer antisense oligonucleotides corresponding to portions of oncogenes preferably selected from the group consisting of ras, raf, cot, mos, myc, preferably c-raf-1, or a growth factor PDGF, FGF, EGF), as an adjunct to radiotherapy, in order to radiosensitize cancer cells to the effects of radiation. Preferably, such oligonucleotides will be administered using a cationic liposomal delivery system, more preferably the cationic liposomal delivery systems discussed supra. The bases comprised in said oligonucleotide may be modified or unmodified, and the size of such oligonucleotides will preferably range from 8 to 100 nucleotides; more preferably 12 to 60 nucleotides, most preferably from 15 to 40, or 15 to 25 nucleotides.

It is an even more specific object of the invention to administer oligonucleotides comprising 5'-GTG-CTCCATTGATGC-3' (SEQ ID NO: 1) and/or 5'-CCTGTATGTGCTCCATT-GATGCAGC-3' (SEQ ID NO: 2), preferably encapsulated in a cationic liposome, wherein the bases of said oligonucleotides may be modified or unmodified, as an adjunct to radiotherapy.

DETAILED DESCRIPTION OF THE FIGURES

FIGS. 1A–H: A liposomal encapsulation of ATG-AS raf ODN (SEQ ID NO: 3), 5'-fluorescein-labeled ATG-AS raf ODN was encapsulated in liposomes (PC/CHOL/DDAB) as explained in the experimental procedures. Bright field microscopy of blank liposomes (1a), and fluorescence microscopy of blank liposomes (1b) and liposomes containing the fluorescein-labeled ATG-AS raf ODN (C-H) are shown.

FIG. 2: (a) Time-course of cellular uptake of LE-ATG-AS raf ODN (SEQ.ID NO:3), SQ-20B cells were incubated with $^{32}$P-5' end labeled and an excess of unlabeled LE-ATG-AS raf ODN (10 μM) for indicated times as described in the experimental procedures. Results are mean±s.d from two independent experiments each performed in duplicate. (2b) Intracellular stability of LE-ATG-AS raf ODN. Cells were incubated with $^{32}$P-end labeled and an excess of unlabeled LE-ATG-AS raf ODN (10 μM in 1% FBS containing medium for 1 hour, washed with PBS and then incubations continued in 20% FBS containing medium for 0 hour (lane 2), 2 hours (lane 3), 8 hours (lane 4), 12 hours (lane 5), and 24 hours (lane 6). Cells were lysed and ODNs in various samples were analyzed by denaturing gel electrophoresis as explained in the experimental procedures. Lane 2, radiolabeled control LE-ATG-AS raf ODN; 15-mer, ATG-AS raf ODN; migrations of xylene cyanol (XC) and bromophenol blue (BP) are indicated.

FIG. 3: The plasma concentration-time profile of LE-ATG-AS (SEQ ID NO: 3) raf ODN, 30 mg/kg LE-ATG-AS raf ODN (top panel) or TG-AS raf ODN (middle panel) was administered i.v. in Balb/d nu/nu mice. Blood samples were collected from retro-orbital sinus as indicated times after injection and the ODNs in plasma samples were extracted and analyzed by denaturing gel electrophoresis as explained in the experimental procedures. St standards prepared by spiking known amounts of ATG-AS raf ODN in blank plasma. Top panel: Samples were diluted before electrophoresis as follows: lane 1, 12×; lanes 2 and 3, 4×; lanes 4 and 5, 3.3×; lane 6, 2×; line 7, 1.4×; lane 8, 1.3×; and lane 9, 1×. St lanes represent 0.25, 0.5 and 1.0 μg/ml of ATG-AS raf ODN. 1.0μg/ml of the standard sample corresponds to 18.4, μg of ODN. Additional standards (1.4 to >2 log range) were used to determine ODN concentration over a 24 hour period (data not shown). Middle panel: Samples were diluted before loading as follows: lane 1, 4×, lines 2 and 3, 2×, lanes 4, 5 and 6, 1×; lane 7, 0.75×, lines 8 and 0, 0.6×. St lanes represent 0.125, 0.25, and 0.5 μg/ml of ATG-AS raf ODN, 0.5 μg/ml of the standard sample corresponds to 6.9 ng of ODN. Bottom panel: Plasma concentration-time curve of LE-ATG-AS raf ODN shown in the top panel. Quantification data were calculated based on comparison with known concentrations of the standard samples, and then normalization against sample dilution factors used for loading.

FIG. 4: Tissue distribution profiles of LE-ATG-AS raf ODN (SEQ ID NO: 3). Tissue samples were collected at indicated times after i.v. administration of 30 mg/kg LE-ATG-AS raf ODN. ODNs were extracted from homogenized tissues and probed with $^{32}$P labeled ATG-S raf ODN as explained in the experimental procedures. (4a) Representative autoradiographs from liver and kidney, (b) ATG-AS raf ODN concentration in different tissues at indicated times after a dose of 30 mg/kg LE-ATG-AS raf ODN was administered i.v. Quantification data were calculated based on comparison with known concentrations of the standard samples, and then normalization against the weights of organs collected.

Figure 5:
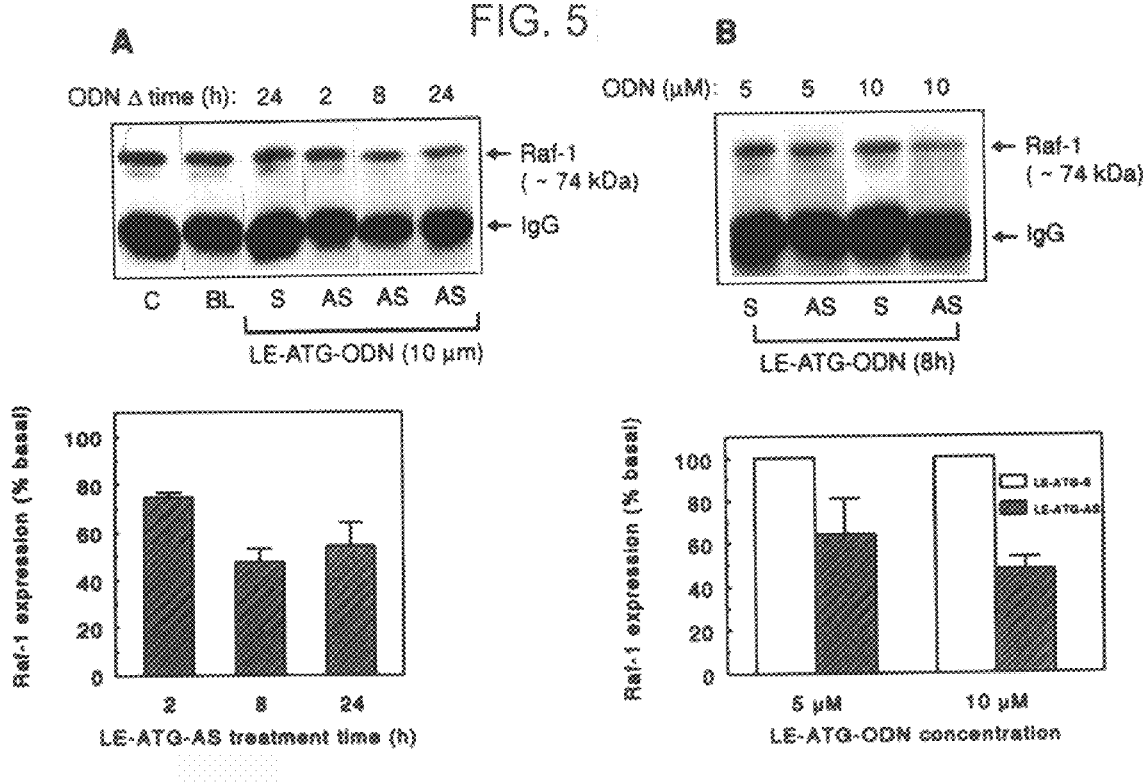

FIG. 5: Specificity of inhibition of Raf-1 protein expression by LE-ATG-AS rad ODN, (5a) Time-course analysis, Logarithmically growing SQ-20B cells were treated with 10 μm of LE-ATG-S raf ODN (AS) (SEQ ID No: 3), or LE-ATG-S rad ODN (S) (SEQ ID No: 1) for indicated times in FBS containing medium. Untreated control cells (C) or cells treated with blank liposomes (10 μm) were simultaneously switched to 1% FBS containing medium for eight hours. Whole cell lysates were normalized for total protein content and immunoprecipitated with agarose-conjugated polyclonal anti-Raf-1 antibody (Santa Cruz). Immune complexes were immunoblotted with polyclonal anti-RAF-1 antibody as described in the experimental procedures (top). Results from three independent experiments were quantified and data are expressed relative to the level of Raf-1 in LE-ATG-S raf ODN-treated cells (bottom ), (5b) Dose-response analysis, Logarithmically growing SQ-20B tumor cells were treated with indicated concentrations of LE-ATG-AS raf ODN (AS) or LE-ATG-S raf ODN (S) in 1% FBS containing medium for eight hours. Normalized cell lysates were analyzed for RAF-1 expression (top). Quantification data from three independent experiments are expressed relative to the level of Raf-1 in LE-ATG-S raf ODN-treated cells (bottom).

Figure 6:
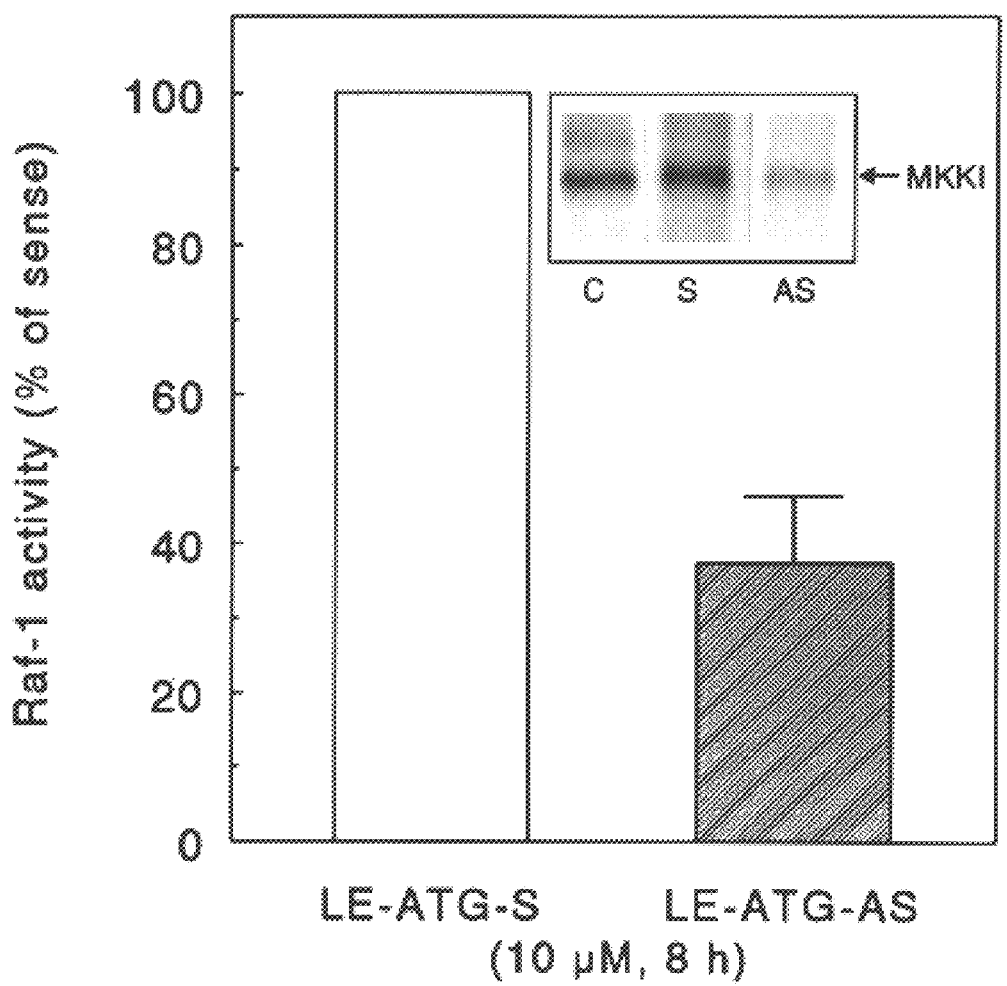

FIG. 6: Inhibition of Raf-1 protein kinase activity by LE-ATG-AS raf ODN (SEQ ID NO: 3), Logarithmically growing SQ-20B cells were treated with 120 $\mu$m LE-ATG-AS raf ODN (AS) (SEQ ID NO: 3), or 10 $\mu$m LE-ATG-S raf ODN (S) (SEQ ID NO: 1) for eight hours in 1% FBS containing medium. Control cells (C) were simultaneously switched to 1% FBS containing medium for eight hours. Whole cell lysates were normalized for protein content, and Raf-1 phosphotransferase activity was assayed in vitro using its physiologic substrate, MKK1 as described in the experimental procedures. Radiolabeled reaction products were separated by electrophoresis, and autoradiographed (inset). Quantification data from two independent experiments, each performed in duplicate, are expressed as Raf-1 enzymatic activity in LE-ATG-AS raf ODN-treated cells relative to LE-ATG-S raf ODN-treated cells.

FIG. 7: Effects of intravenous administration of LE-ATG-AS raf ODN our Raf-1 expression in normal and tumor tissues. Raf-1 expression was examined in liver, kidneys and SQ-20B tumor xenograft of Balb/c nu/nu mice after i.v. injections of 6 mg/kg daily dose of LE-ATG-AS raf ODN (AS) (SEQ ID NO: 3) or LE-ATC-S raf ODN (S) (SEQ ID NO: 1) for five consecutive days. Control mice (C) received normal saline. Representative data showing Raf-1 expression in lysates normalized for protein content by immunoprecipitation and immunoblotting (top). Quantification data are shown as mean±s.d from three mice (bottom).

Figure 8:
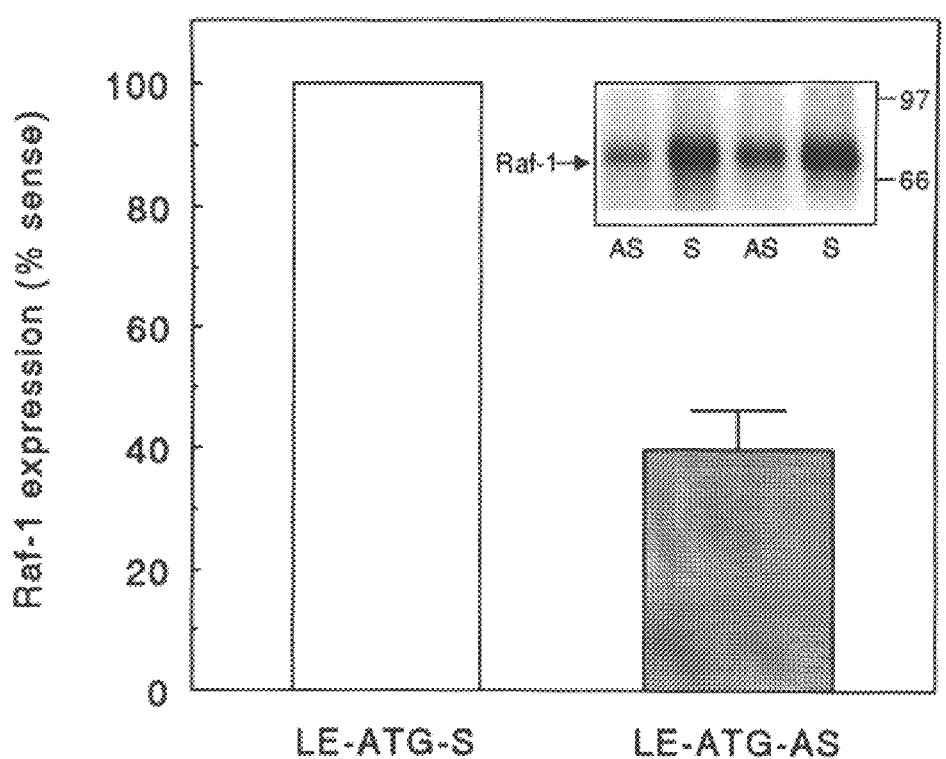

FIG. 8: Inhibition of Raf-1 protein expression in SQ-20B tumor xenografts by intratumoral administration of LE-ATG-AS raf ODN: Each animal received intratumoral injections of LE-ATG-AS raf ODN (AS) (SEQ ID NO: 3) on the right flank and LE-ATG-S raf ODN (S) (SEQ ID NO: 1) on the left flank at a dose of 4 mg/kg daily for seven days as explained in the experimental procedures. Raf-1 expression in the right (AS) and left (S) tumor xenografts from two representative animals is shown (inset). Quantification data shown are mean±s.d., from three representative mice.

Figure 9:
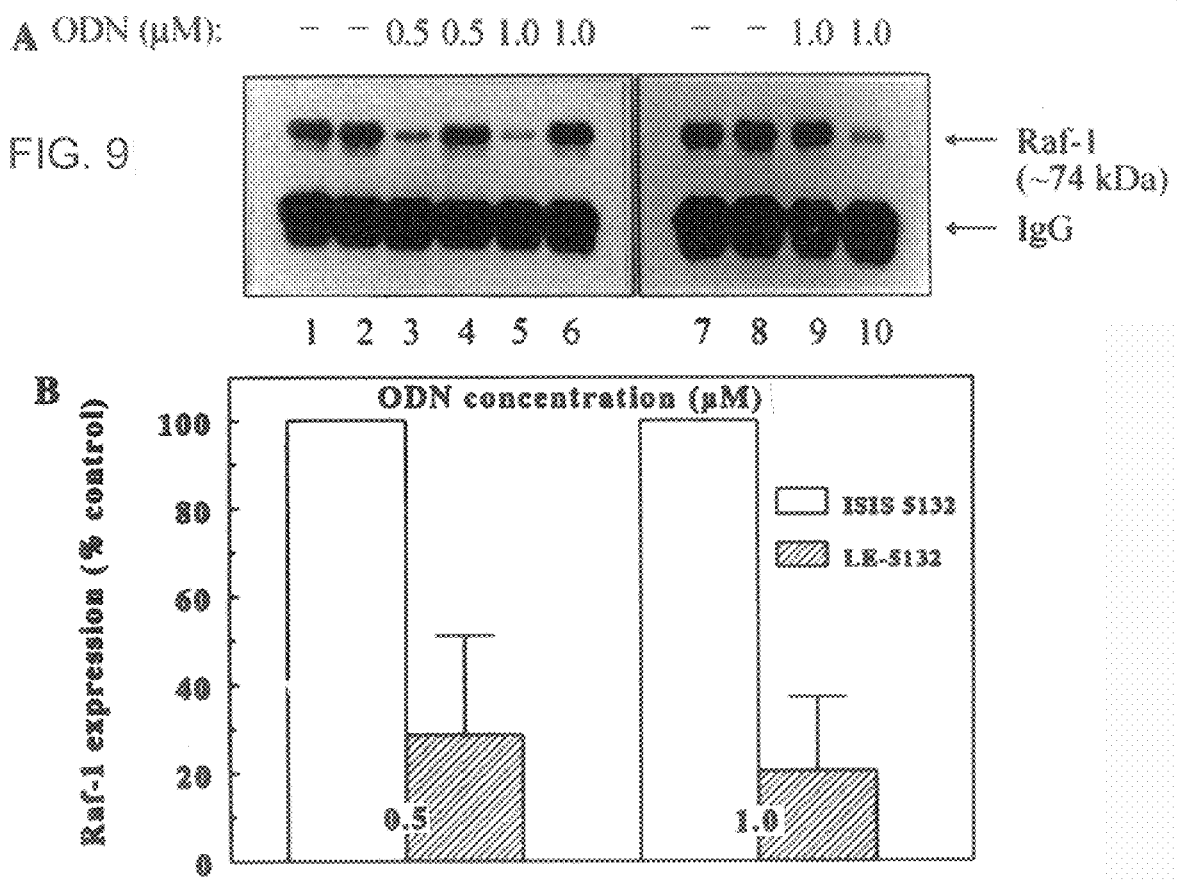

FIG. 9: Antisense sequence-specific inhibition of Raf-1 expression in SQ-20B cells. (9A) Logarithmically growing SQ-20B cells were treated with indicated ODN concentrations of LE-5132 (lanes 3, 5 and 10), 5132 (lanes 4 and 6), or LE-10353 (lane 9) as described in Materials and Methods. Control cells were either left untreated (lanes 1 and 7) or treated with 1 $\mu$M blank liposomes (BL) (lanes 2 and 8). Whole cell lysates were normalized for total protein content and immunoprecipitated with agarose-conjugated polyclonal anti-Raf-1 antibody. Immune complexes were resolved by 7.5% SDS-PAGE and immunoblotted with polyclonal anti-Raf-1 antibody. (B) Data from three independent experiments were quantified and expressed relative to the level of Raf-1 in untreated cells.

Figure 10:
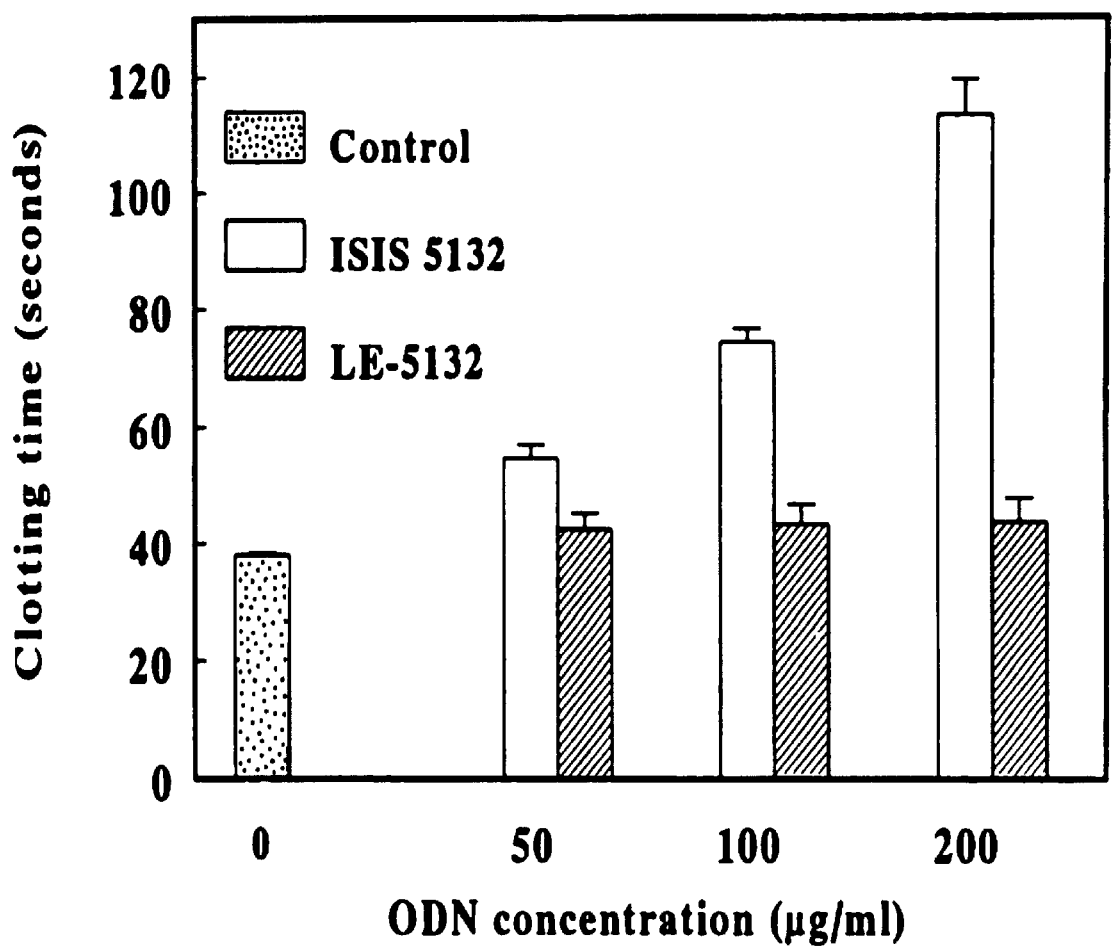

FIG. 10: Effect of LE-5132 on coagulation time. Normal human plasma was mixed with indicated concentration of LE-5132 or 5132 or left untreated and incubated with APTT reagent (purified rabbit brain cephalin extract with allergic acid activator) for one minute at 37° C. The coagulation reaction was initiated by adding calcium chloride, and the time required to form visible clot was recorded mutually in seconds. Data represents mean=SD from three experiments.

FIGS. 11A–C: The plasma concentration-time profile of LE-5132 and 5132; 30 mg/kg LE-5132 or 5132 was administered i.v. in Balb/c nu/nu mice. Blood samples were collected from the retroorbital sinus at indicated times after injection, and ODN in plasma samples was extracted and analyzed by denaturing gel electrophoresis as described. S1, S2 and S3, standards prepared by spiking known amounts of 5132 in blank plasma. (11A) Samples were diluted before electrophoresis as follows: lane 1. 15×; line 2, 10×; lanes 3 and 4, 5×; lane 5, 1×; lanes 6–9, 0.8×. (11B) Samples were diluted before electrophoresis as follows: lane 1, 15×; lane 2, 10×; lanes 3 and 4, 5×; lane 5, 1×; lanes 6–9, 0.8×; S1, S2, and S3 represent 0.25, 0.5, and 1.0 $\mu$g/ml of 5132, respectively; 1.0 $\mu$g/ml of the standard sample corresponds to 20 ng of ODN. (11C) Plasma concentration-time curve of LE-5132 and 5132. Quantification data were calculated based on comparison with known concentrations of the standard samples and then normalized against sample dilution factors used for loading.

Figure 12:
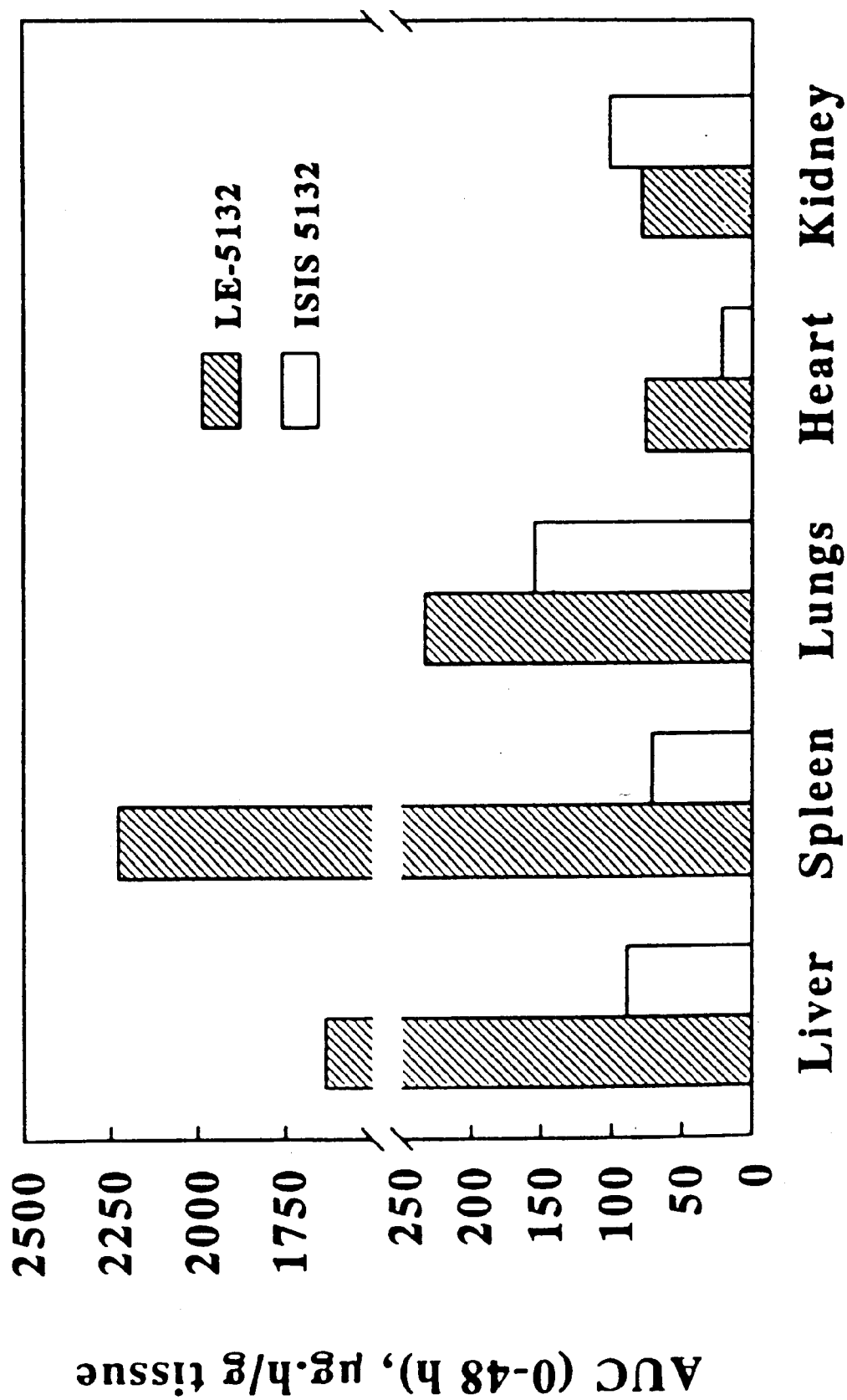

FIG. 12: Normal tissue pharmacokinetics of LE-5132/5132 as a function of area under the concentration-time curve (AUC). Tissue samples were collected between 0 and 48 hours after administration of 30 mg/kg LE-5132 or 5132 as in FIG. 11. ODN were extracted from homogenized tissues and probed with ($^{32}$P)-labeled sense raf ODN. Quantification analysis was performed based on comparison with known concentration of the standard samples and then normalized against the weights of the organs collected.

Figure 13:
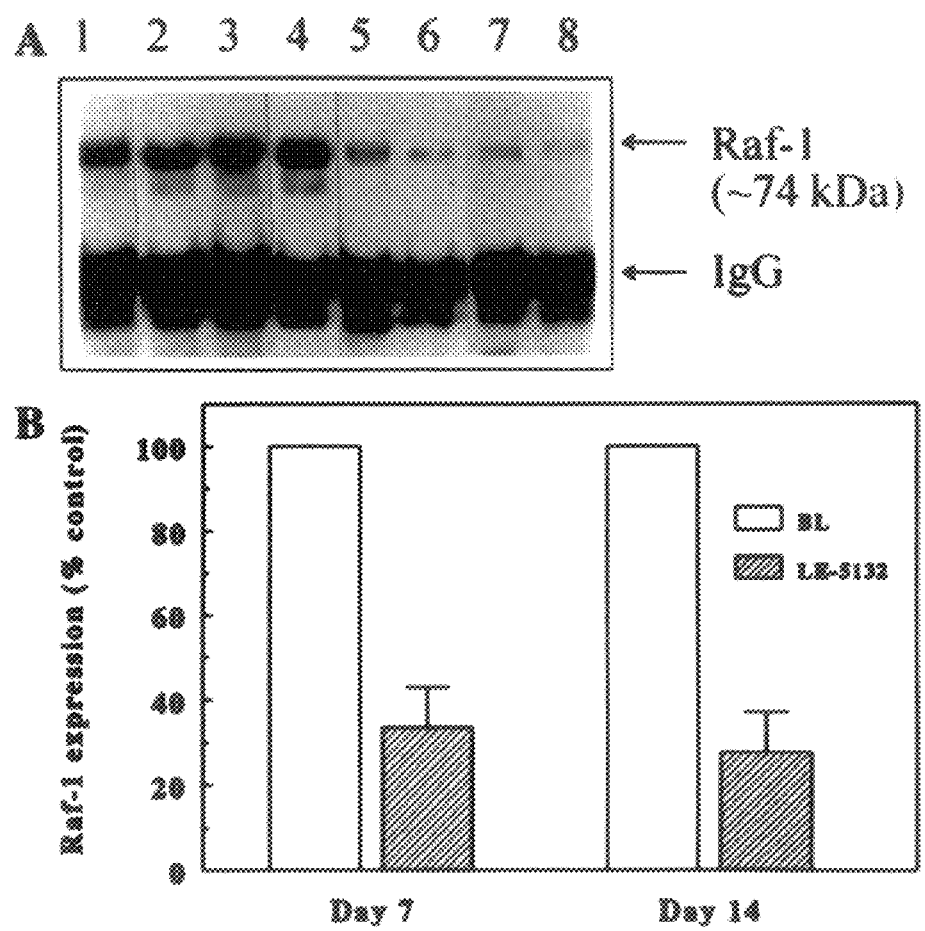

FIG. 13: Effect of LE-5132 on SW-20B tumor growth. SQ-20B tumor cells (2×10$^6$) were injected a.c. into the left flank region of each male Balb/c nu/nu mouse. 10–12 weeks old. Tumor xenografts were grown to a mean tumor volume of 94±6.4 mm$^3$, and the animals were randomized into two treatment groups. Day 0 represents the first day of treatment. Mice were given i.v. 6 mg/kg LE-5132 or blank liposomes (BL) once daily for the first 7 days, followed by six additional doses on alternate days, as indicated by the arrows. The animals were killed on day 30. The data shown are mean±SE of 5–7 animals per group.

Figure 14:
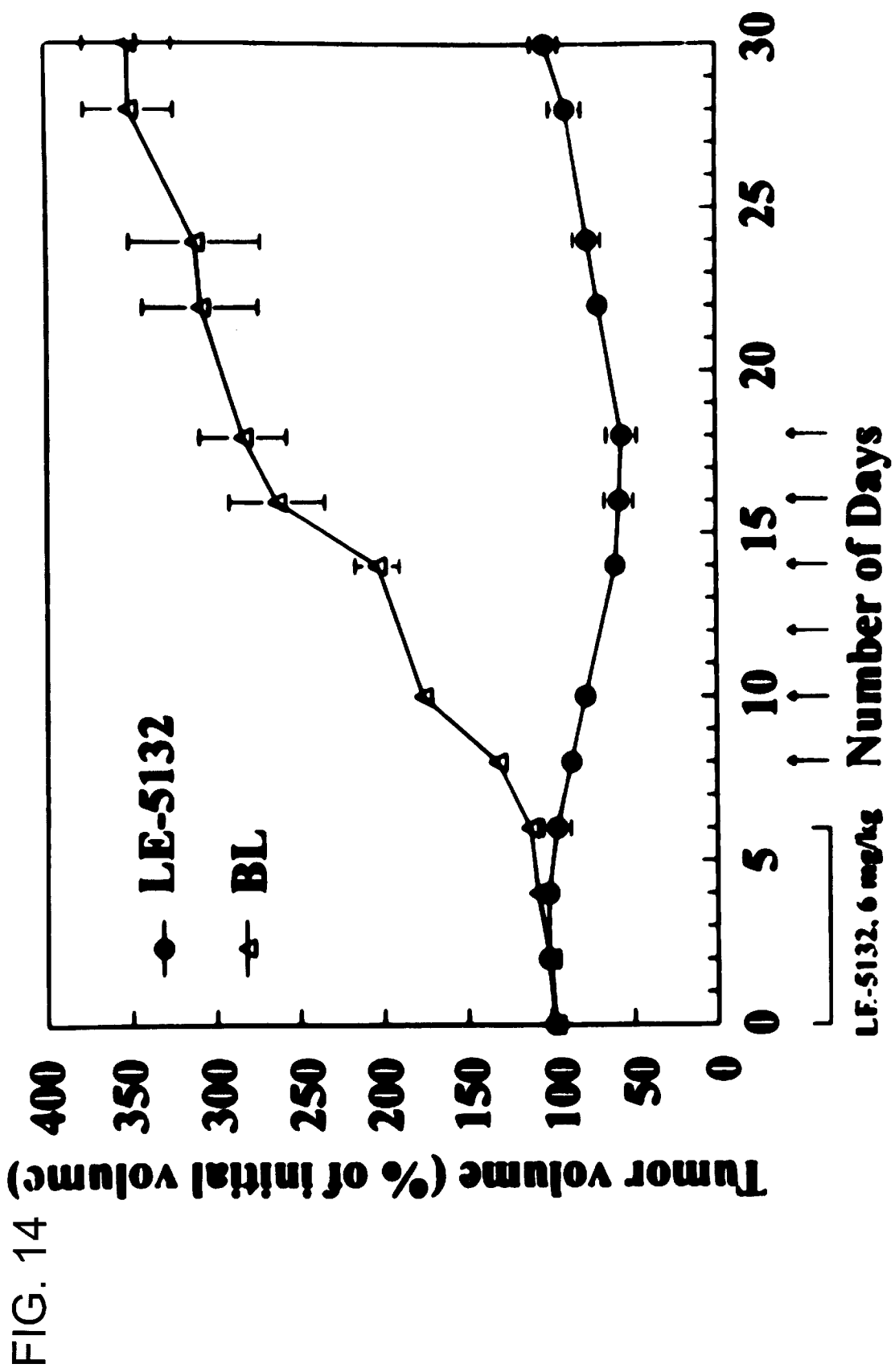

FIG. 14: Effect of LE-5132 on Raf-1 protein level in SQ-20B tumors. (14A) Tumor-bearing mice were treated with LE-5132 (i.v., 10 mg/kg) or IR (3.8 Gy/day) or both, as explained in the legend to FIG. 7. Tumors representing various treatment groups were excised on day 7 (lanes 1 and 2) and day 14 (lanes 3–8) of treatment. Raf-1 expression was detected in tissue homogenates normalized for protein content by immunoprecipitation, followed by immunoblotting. Lane 1, untreated control; lanes 2 nd 3, BL; lane 4, IR; lanes 5 and 6, LE-5132; lanes 7 and 8, LE-5132+IR, (14B) Quantification data shown are mean±SE from 2 animals.

FIGS. 15A–B: Effect of LE-5132 and ionizing radiation on SQ-20B tumor growth. (15A) SQ-20B tumor xenografts were grown in male Balb/c nu/nu mice as described. Animals bearing a mean tumor volume of 72.0±4.3 mm$^3$ were randomized into five treatment groups. Day 0 represents the first day of treatment. Mice were treated with LE-5132 10 mg/kg i.v. (LE-5132), ionizing radiation once a day with 3.8 Gy (IR), or a combination of these two treatments for the indicated days (LE-5132+IR). Control groups received either blank liposomes (BL) or no treatment (C). Animals were killed on day 45. The data shown are mean±SE of 5–7 animals per group. (15B) Fold change in mean tumor volumes in different treatment groups on day 30. The data shown are mean±SE from two independent experiments. 5–7 animals per group per experiment. ⁻$p<0.001$.

FIGS. 16A–D: Histopathology of SQ-20B tumors. Tumors were excised 24 hours after the final treatment.

Shown are examples of the histopathology of an untreated tumor (16A) and tumor treated with LE-5132 (16B), IR (C), or LE-5132+IR (16D). ×250.

Figure 17:
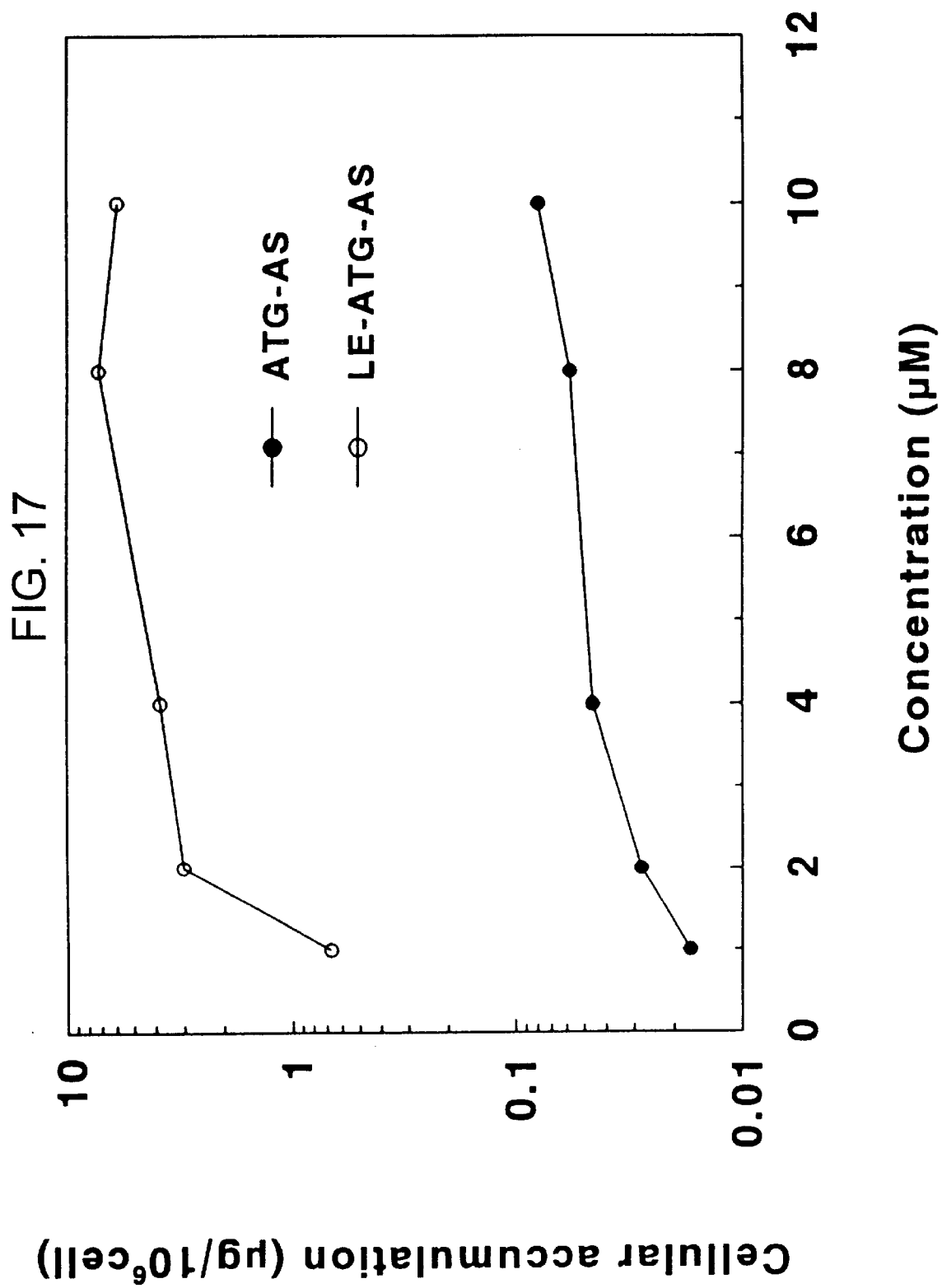

FIG. 17: contains in vitro results of dose-response uptake experiment using unlabeled antisense raf oligo (ATG-AS) (SEQ ID NO: 3) in free (ATG-AJ$^c$) or liposome (DMTAP= PC=CHOL) encapsulated from (LE-ATG-AS).

Figure 18:
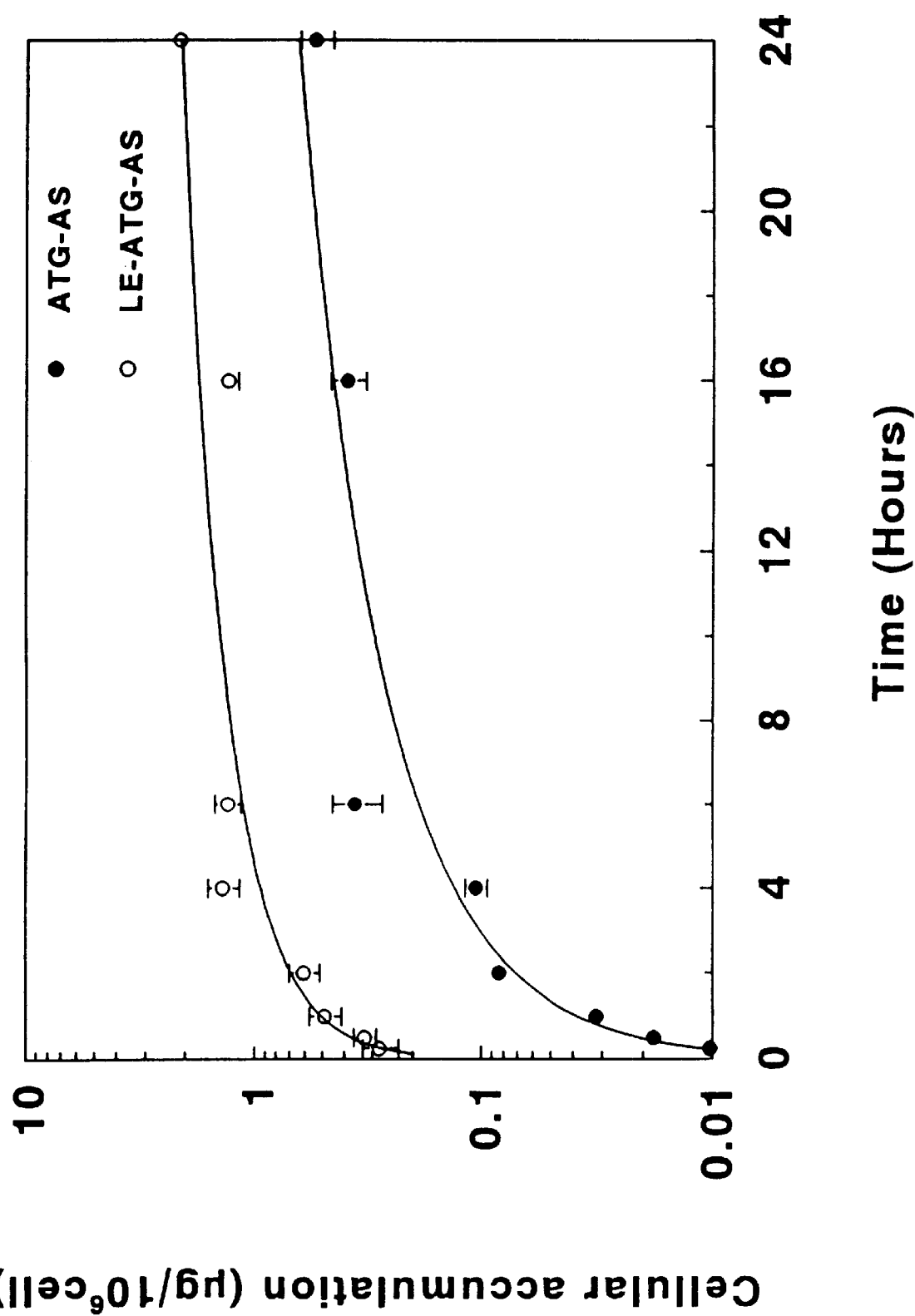

FIG. 18: contains results of time-course uptake experiment in SQ-20B timer cells using free (ATG-AS) (SEQ ID NO: 3) or liposome encapsulate (LE-ATG-AS) raf oligonucleotides.

Figure 19:
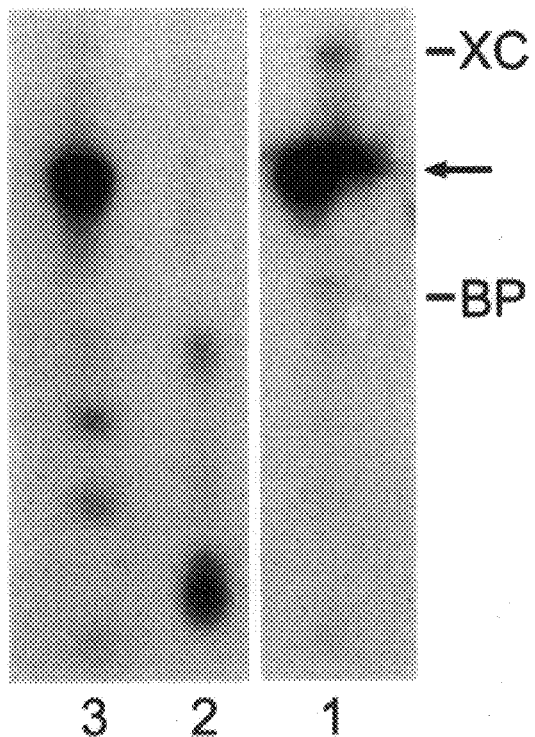

FIG. 19: contains half of stability experiment comparing stability of raf oligonucleotides in free (ATG-AS) (SEQ ID NO: 3) or liposome encapsulate (LE-ATG-AS) μm.

Figure 20:
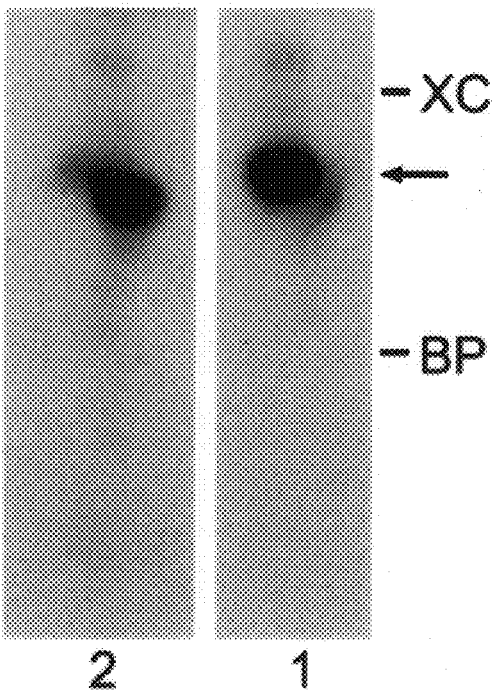

FIG. 20: contains results of another stability experiment comparing stability of free raf oligonucleotides (ATG-AS) (SEQ ID NO: 3) or liposome encapsulate (LE-ATG-AS).

Figure 21:
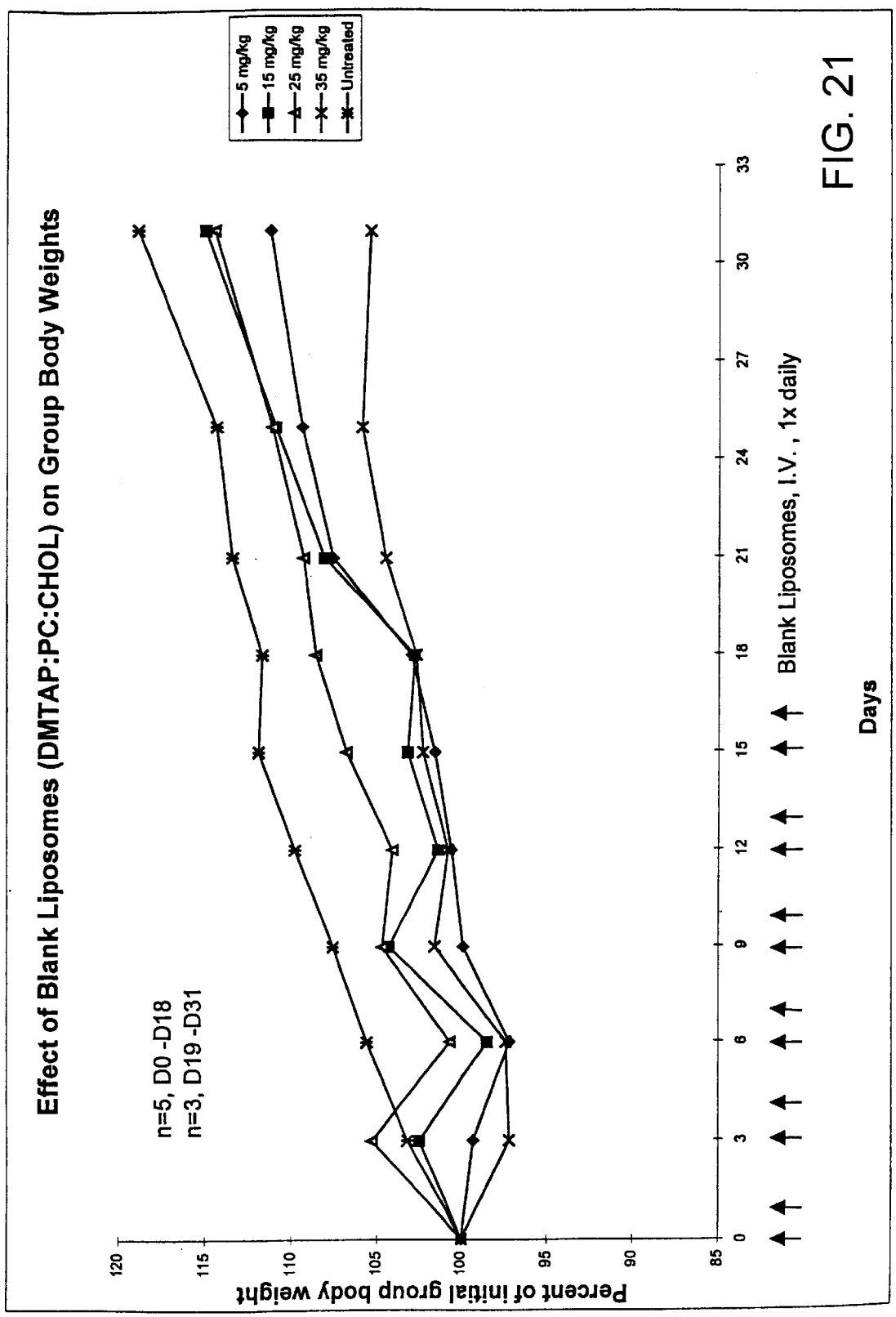

FIG. 21: contains survival data in mice/CD2F1 mice administered DMTAP:PC: CHOL liposomes injected i.v.

Figure 22:
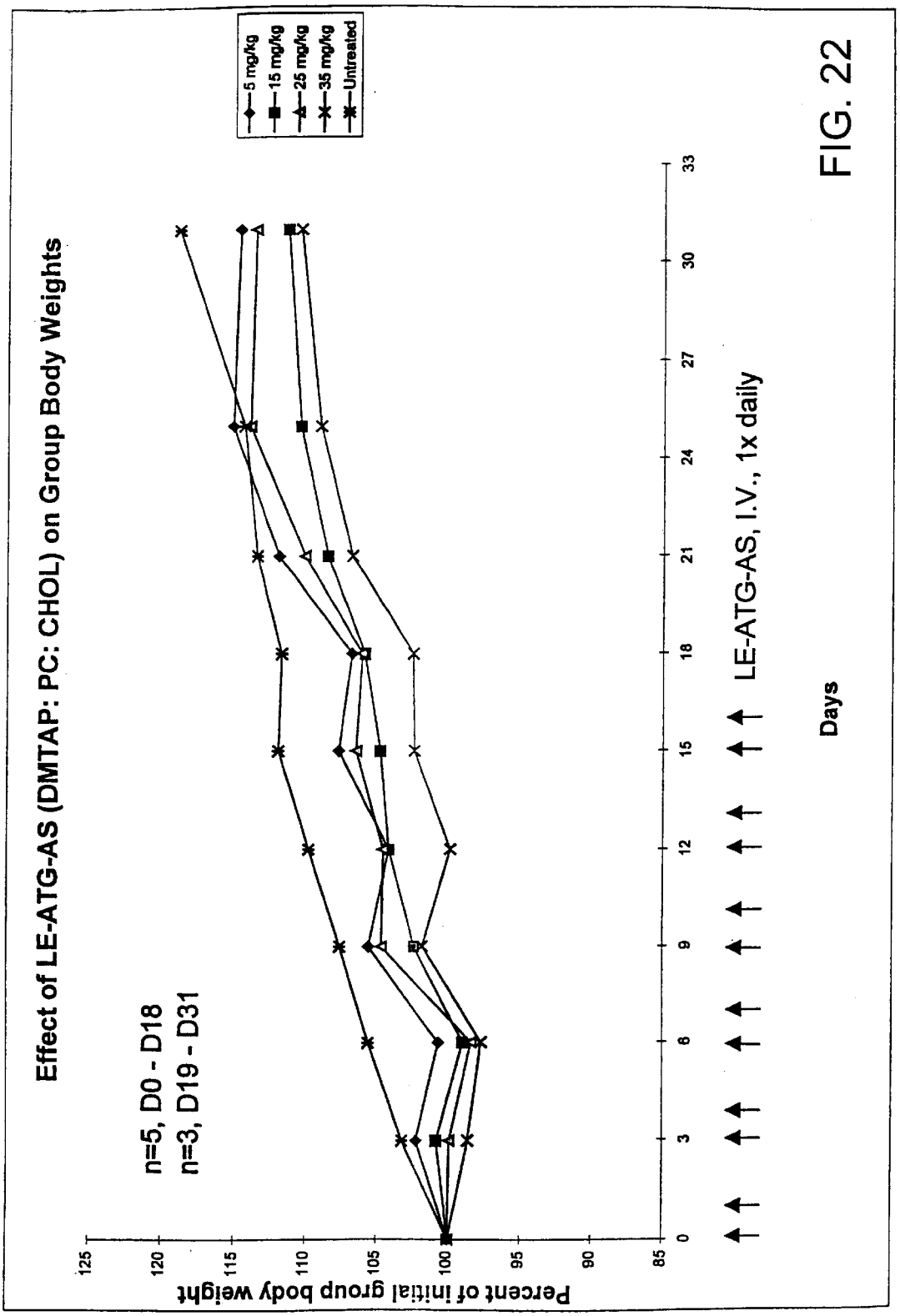

FIG. 22 contains survival data from mice CD2F1 mice administered raf oligonucleotides encapsulate in DMTAP-:PC:CHOL liposome (LE-ATG-AS) (SEQ ID NO: 3).

DETAILED DESCRIPTION OF THE INVENTION

In a first embodiment, the present invention relates to a novel cationic liposomal formulation and in vivo use thereof as a therapeutic or diagnostic agent. Specifically, the present invention relates to the preparation of a cationic liposome comprised of at least one cationic lipid selected from the group consisting of dimethyldioctadecyl ammonium bromide (DDAB), 1,2-dimyristoyl-3-trimethyl ammonium propane (DMTAP), N-2,3-(dioleoyloxy)propyl)-N,N,N-trimethylammoniumchloride, 1-[2-(9(Z)-octadecenoyloxy)-ethyl]-2-(8(Z)heptadecenyl)-3-(2-hydroxyethyl)-imidazolinium chloride; 1,2-(dioleoyl-3 -trimethyl ammonium propane (DOTAP), in combination with phosphatidylcholine (PC) and cholesterol (CHOL). Preferably, the molar ratio of cationic lipid:phosphatidylcholine:cholesterol will range from 0.5 to 2.5:2.0 to 4.0:0.5 to 0.5 to 2.5, more preferably 0.7 to 1.5:2.5 to 3.5 and 1.0 to 2.0; and most preferably 0.8 to 1.2:3.0 to 3.6 and 1.4 to 1.8.

An especially preferred molar ratio for cationic lipid-:phosphatidylcholine:cholesterol is about 1:3.2:1.6. The subject cationic liposomes can be prepared by known methods. A preferred method is described in the Examples infra. Essentially, such method comprises dissolving lipids in a solvent (e.g., chloroform or methanol), evaporation to dryness, hydration at low temperature, addition of an active agent (e.g., oligonucleotide) in phosphate buffered saline (PBS), vigorous vortexing and sonication, and removal of unencapsulated oligo. These methods have been found to provide for high entrapment efficiencies (90% or higher) The resultant liposome encapsulated oligos can be stored, e.g. at 4° C. and used thereafter. For example, in the case of liposome encapsulated oligos, the liposomes can be stored for at least about 2 weeks.

The cationic liposomes of the present invention can be used to encapsulate a desired agent, e.g. an oligonucleotide, peptide or protein (e.g., antibody, growth factor, cytokine, enzyme hormone, receptor or fragment), drug or chemotherapeutic agent, radionuclide, oligosaccharide, fluorophore, diagnostic agent (such as a radionuclide, detectable enzyme or flourophore). In the preferred embodiment, the subject cationic liposomes will be used to encapsulate an oligonucleotide, preferably an antisense oligonucleotide, and even more preferably an antisense oligonucleotide corresponding to an oncogene such as raf.

As shown in the examples, it has been found that cationic liposomes according to the invention provide for high encapsulation efficiencies, protect oligonucleotides from being degraded in plasma, for prolonged periods (i.e., 8 hours or longer), are effectively delivered to target cells and enhance intracellular availability of intact oligonucleotides.

The present invention may obviate the need to modify the bases in the encapsulated oligonucleotide to enhance such inability. However, the present invention embraces the use of oligonucleotides that do or do not comprise modified bases e.g. modifications to the phosphorothioate backbone, such as phosphorothioate modified oligos, and lipophilic modified oligos (e.g. cholesterol or poly-L-lysine).

Preferably, the oligonucleotide will be an antisense oligonucleotide corresponding to an oncogene such as raf, ras, cot, mos, myc, myb, erb-2, or part of a viral gene, and will inhibit expression of a gene that is involved in cancer or viral infection. In preferred embodiments, these liposome encapsulated oligonucleotides will be used in the treatment or diagnosis (e.g., in vivo imaging ) of cancer or viral infection. For example, the oligonucleotide of many comprised a portion of a viral gene from a virus such as HIV-1, HIV-2, HPV, CMV, herpes, influenza, hepatitis, RSV. For example, the oligonucleotide may correspond to a portion of the env, gal or pol gene of HIV-1 or HIV-2.

Also, the subject liposomes may be used to encapsulate peptides, e.g., haptenic peptides, proteins, antibodies hormones, growth factor and fragments thereof, chemotherapeutic agents, radionuclides, oligosaccharides, lectins, receptors, cytokines or monokines, antineoplastic agents, and other active agents. Examples thereof include by way of example interleukins, interferons ($\alpha,\beta,\gamma$), colony stimulating factors, tumor necrosis factor, methotrexate, cisplatin, doxorubicin, daonorubicin, fibroblast growth factor, and platelet derived growth factor.

Examples of radionucleotides include by way of example radioactive species of yttrium, indium, and iodine.

The amount of active agent that is encapsulated in the subject liposome will at most be an amount that maintains liposome stability after encapsulation. In the case of oligonucleotides, the amount of oligonucleotide will range from a about 0.1 to 1,000 μg oligo/mg of lipid, more preferably about 1 to 100 μg oligo/mg of lipid, and most preferably about 10 to 50 μg oligo/mg of lipid.

However, this amount may vary with different active agents. The subject liposomes will be administered in combination with a pharmaceutically acceptable carriers such as glucose, and saline phosphate buffered saline. Also, the liposomes may include preservatives, emulsifiers or surfactants often used in the formulation of pharmaceuticals.

The subject active agent containing liposomes may be administered by different methods. Systemic and non-systemic methods of administration are suitable. Such methods include an injection (intramuscular, intraarterial, intraperitoneal, intravenous, intratumoral or other site-specific injection, intrathecal, inhalatories, oral administration, and topical methods. Preferred methods of administration include intratumoral and intravenous methods of administration.

The dosage effective amount will depend upon the encapsulated agent, the disease or condition treated, the patient treated, other therapies, and other known factors. In the case of oligonucleotides a topical dosage will be one ranging from about 0.1 μg to about 500 μg. Typically, an amount will be administered that results in blood serum concentrations of oligo or other agents ranging from about 0.1 μg to 1000 μg/ml.

In a second embodiment of the invention, it has been surprisingly discovered that oligonucleotides, e.g. antisense oligonucleotides can be administered as an adjunct to radiotherapy, preferably in the treatment of cancer that are resistant to radiotherapy. In particular, it has been surprisingly discovered that antisense oligonucleotides, e.g. that correspond to oncogenes such as raf, can be used to enhance the sensitivity of tumor cells to radiotherapy, thereby enhancing efficacy. While not wishing to be bound thereby, it is theorized that such oligonucleotides may render tumor cells more susceptible to lysis or apoptosis (programmed cell death).

Specifically, this has been demonstrated with raf antisense oligonucleotides. In this embodiment of the invention, an antisense oligonucleotide corresponding to an oncogene such as raf will preferably be administered in liposome encapsulated form, prior, concurrent, or shortly after ionizing radiation therapy.

Irradiation will be effected by known methods, e.g., by use of a $[M_{Cs}]$ irridation, or other suitable device for delivering irradiation to tumor sites. The amount of irradiation will be an amount sufficient to provide for tumor regression or remission. As substantiated by the results, it has been found that the combined use of antisense oligonucleotide and radiation has a synergistic effect on tumor remission, especially on tumors resistant to radiation. Therefore, the present invention may enable use of lower dosages of radiation than for previous therapies. However, of course, the amount of radiation will depend upon factors including the condition of the patient, weight, any other therapies, etc. Selection of suitable radiation dosages and therapeutic regimens is well within the purview of the ordinary skilled artisan.

The size of the administered oligonucleotide will preferably be no more than 100 nucleotides, more preferably no more than 40 nucleotides, or from about 8 to 40 nucleotides and more preferably from about 15 to 40 or 15 to 25 nucleotides. The size of the antisense oligonucleotide is one such that upon in vivo administration it results in an anti-tumor effect, by disrupting a gene, the expression of which is involved in tumor growth, metastasis or apoptosis, or which sensitizes tumor cells to radiotherapy.

EXAMPLE 1

Materials and Methods
Oligodeoxyribonucleotides

Oligodeoxyribonucleotide sequences directed toward the translation initiation site of human c-Raf-1 cDNA were synthesized at L of strand Labs Limited (Gaithersburg, Md., USA) using beta-cyanoethyl phosphoramidite chemistry on a Biosearch 8750 DNA synthesizer. The sense (ATG-S) and antisense (ATG-AS) Raf-1 ODN sequences were 5'GCAT-CAATGGAGCAC-3' and (SEQ ID NO:3) 5'-GTG-CTCCATTGATGC-3', (SEQ ID NO: 1) respectively. One terminal base linkage at each end was modified to a phosphorothioate group using 3H-1,2-benzo-dithiole-3-1,1,1-dioxide as the sulfurizing agent. Oligos were synthesized at the 15 μm scale and purified on reverse phase chromatography columns. For quality control, a small aliquot of each oligo preparation was $^{32}$P-end-labeled and visualized by polyacrylamide gel electrophoresis (20% acrylamide and 5% bis) followed by densitometric scanning of the labeled products.

For synthesis of the 5'-fluorescein-labeled ATG-AS/S raf ODN, the 3' and 5' base linkages were modified to phosphorothioate groups as mentioned above. Fluorescein phosphoramidite (1-dimethoxytriyloxy-2-(N-thiourea-(di-O-pivaloyl-fluorescein)-4-aminobutyl-propyl-3-O-(2-cyanoethyl)-(N,N-diisopropyl)-phosphor-amidite) was coupled to the 5' ends during the last three synthesis cycles. The coupling consisted of the simultaneous addition of, and 15 min incubation with 0.25 ml of a 0.1 M solution of fluorescein amidite in acetonitrile and 0.25 ml of a 0.45 M solution of tetrazole in acetonitrile. After synthesis, the ODNs were deprotected and cleaved from the support in 1.0 ml 30% ammonium hydroxide for 24 h at room temperature. During deprotection, the fluorescein labels were modified to the same structure as when prepared using fluorescein isothiocyanate (FITC). Purification was performed using standard reverse phase chromatography cartridges. The purified ODNs were eluted from the cartridges in 1.0 ml 20% acetonitrile, dried and resuspended in water.

Preparation of Cationic Liposomes

Cationic lipids, 1,2-dioleoyl-3-trimethyl ammonium propane (DOTAP), 1,2-dimeyristoyl-3-trimethyl ammonium propane (DMTAP), and dimethyldioctadecyl ammonium bromide (DDAB) were purchased from Avanti Polar Lipids (Alabaster, Ala., USA). Blank liposomes were prepared using one of the three cationic lipids, phosphatidylcholine (PC) and cholesterol (CHOL) in a molar ratio of 1:3.2:1.6. LE-ATG-S and LE-ATG-AS raf ODNs were prepared using DDAB, PC and CHOL in a molar ratio of 1:3.2:1.6. Briefly, the lipids dissolved in chloroform or methanol were evaporated to dryness in a round-bottomed flask using a rotatory vacuum evaporator. The dried lipid film was hydrated overnight at 4° C. by adding 1 ml of ODN at 1.0 mg/ml in phosphate-buffered saline (PBS). The film was dispersed by vigorous vortexing and the liposome suspension was sonicated for 5 min in a bath type sonicator (Laboratory Supplies, Hicksville, N.Y., USA). The ODN to lipid ratio was 30 μg ODN/mg of lipid. The unencapsulated ODN was removed by washing the liposomes and centrifugation three times at 25000 g for 30 min in PBS. The ODN encapsulation efficiency was determined by scintillation counting of an aliquot of the preparation in which traces of $^{32}$P-end-labeled ODN were added to an excess of the unlabeled ODN. The liposome-encapsulated ODNs were stored at 4° C. and used within 2 weeks of preparation. Blank liposomes were prepared exactly as described above in the absence of ODN.

Cell Culture

SQ-20B tumor cells were established from a laryngeal squamous cell carcinoma of a patient who had failed a full course of radiation therapy.[43] Tumor cells were grown as monolayers in Dulbecco's modified Eagle's medium (GIBCO BRL, Grand Island, N.Y., USA) supplemented with 20% heat inactivated fetal bovine serum (FBS), 2 mM glutamine, 0.1 mM nonessential amino acids, 0.4 μg/ml hydrocortisone, 100 μg/ml streptomycin and 100 U/ml penicillin.

Intracellular raf ODN Uptake and Stability Assays

Logarithmically growing SQ-20B cells were seeded into six-well plates (1×10$^6$ cells per well) in 20% FBS containing medium. The next day, cells were switched to 1% FBS containing medium and incubated at 37° C. with 10 μM $^{32}$P-labeled LE-ATG-AS raf ODN or ATG-AS raf ODN (1×10$^6$ c.p.m./ml). Following incubation for various intervals, cells were washed with PBS, trypsinized and centrifuged. The cell pellet was rinsed twice with PBS, resuspended in 0.2 M glycine (pH 2.8) and then washed again with PBS. This treatment strips off the membranebound ODN, and the remaining radioactivity was interpreted as representative of the intracellular level of ODN. The cell pellet was then lysed in 1% SDS and the intracellular radioactivity was determined by liquid scintillation counting.

For ODN stability studies, cells were seeded and incubated with 10 μM $^{32}$P-labeled LE-ATG-AS raf ODN or ATG-AS raf ODN (1×106 c.p.m./ml) for 4 h at 37° C. in 1% FBS containing medium. Following this initial incubation with ODN, cells were washed three times with PBS and switched to 20% FBS containing medium. Incubations continued for various times, followed by trypsinization and washing with PBS. The cell pellets were lysed in 10 mM Tris-HCl, 200 mM NaCl, 1% SDS, 200 ,g/ml proteinase K, pH 7.4 for 2 n at 37° C. ODNs were extracted with phenol:chloroform, and the aqueous fractions were collected and aliquots were analyzed by scintillation counting. The samples were normalized for equal radioactivity in order to correct for a possible ODN efflux over time, followed by electrophoresis in a 15% polyacrylamide/7 M urea gel, and autoradiography.

Pharmacological Disposition Studies of raf ODN

Male Balb/c nu/nu mice (Charles River, Raleigh, N.C., USA; 10–12 weeks old) were maintained in the Research Resources Facility of the Georgetown University according to accredited procedure, and fed purina chow and water ad libitum. Mice were injected intravenously via the trail vein with 30 mg/kg of LE-ATG-AS raf ODN or ATG-AS raf ODN. At 5 min, 15 min, 30 min, 1 h, 2 h, 4 h, 8 h, 24 h and 48 h after injection, one animal in each group was bled from the retro-orbital sinus into heparinized tubes under anesthesia, and killed by cervical dislocation. The blood was centrifuged immediately at 300 g for 10 min at 4° C. to separate the plasma. The liver, kidneys, spleen, heart and lungs were rapidly excised and rinsed in ice-cold normal saline. The plasma and organs were stored at −70° C. until further analysis.

Antisense raf ODN was isolated from plasma samples using the phenol-chloroform extraction method, and from tissues using a DNA extraction kit (Stratagene, La Jolla, Calif., USA). The raf ODN concentration standards were prepared by adding known amounts of ATG-AS raf ODN in blank plasma or blank tissue samples, followed by extraction as mentioned above. The extracts were loaded on to 20% polyacrylamide/3 M urea gels and electrophoresed in TBE buffer. The gels were electroblotted on to nylon membranes in 0.5×TBE buffer at 20 V for 1 h, and the blots were probed with $^{32}$P-labeled sense probe (ATG-S raf ODN) in Quickhyb buffer (Stratagene) at 30° C. overnight. The radiolabeled probe was generated by 5'-end-labeling of ATG-S' raf ODN with γ-$^{32}$-P-ATP using T4 polynucleotide kinase and purification over Chroma Spin-10 columns (Clontech, Palo Alto, Calif., USA). A 10- to 50-fold excess of the probe was used to ensure saturation of all bands. The autoradiographs were scanned using a computer program (ImageQuant software, Molecular Dynamics, Sunnyvale, Calif., USA), and the amounts of ATG-AS raf ODN in various samples were calculated by comparison to standards.

In vivo Delivery of S/AS raf ODN

Logarithmically growing SQ-20B cells were injected subcutaneously (2×10$^6$ cells) in the flank regions on both sides in male Balb/c nu/nu mice under mild anesthesia. Tumors were allowed to grow to a mean tumor volume of 115 mm$^3$ before initiation of ODN treatment. Two treatment routes were followed: intravenous and intratumoral. For intravenous delivery, mice were randomly divided into six groups. Three mice in each group received LE-ATG-AS, LE-ATG-S, ATG-AS, ATG-S, blank liposomes or normal saline intravenously by bolus infusion via tail vein at a dose of 6 mg/kg daily for 5 days. Mice were killed 24 h after the last treatment, and the organs and tumor tissue were rapidly excised, rinsed in ice-cold normal saline and stored at −70° C.

For intratumoral delivery, mice were randomly divided into three groups. Three mice in one group received intratumoral injections of 4 mg/kg LE-ATG-AS raf ODN on the right flank, and LE-ATG-S raf ODN on the left flank, daily for 7 days. Two control groups, three mice per group, received normal saline or blank liposomes. Mice were killed 24 h after the last treatment, and the tumor tissue was excised, rapidly rinsed in ice-cold normal saline and stored at −70° C.

Raf-1 Immunoprecipitation and Immunoblotting Assays

For in vitro experiments, logarithmically growing SQ-20B cells were exposed to LE-ATG-AS raf ODN, LE-ATG-S raf ODN or blank liposomes for various doses and time intervals in 1% FBS containing medium. Following incubation, cells were lysed in the buffer containing 500 mM Hepes (pH 7.2), 1% NP-40, 10% glycerol, 5 mM sodium orthovanadate, 1 mM phenylmethysulfonyl fluoride, 20 4g/ml leupeptin. The lysates were clarified by centrifugation at 16000 g for 20 min and the protein concentrations were determined (Pierce, Rockford, Ill., USA). Whole cell lysates, normalized for protein content, were used for immunoprecipitation of Raf-1 using protein A-agarose conjugated rabbit polyclonal antibody against 12 carbosy terminal amino acids of human Raf-1 p74 (Santa Cruz Biotechnology, Santa Cruz, Calif., USA). The immunoprecipitates were sequentially washed with cell lysis buffer, 0.5 M LiCl 100 mM Tris-HCl, pH 7.4, and 10 mM Tris-HCl, pH 7.4. The immune complexes were boiled in Laemmli sample buffer and resolved by 7.5% SDS-PAGE, followed by immunoblotting with polyclonal anti-Raf-1 antibody and detection of Raf-1 using ECL reagents according to the manufacturer's protocol (Amersham Corporation, Arlington Heights, Ill. USA). Raf-1 protein expression was quantified using the computer software program (Image-Quant; Molecular Dynamics, USA).

For in vivo expression studies, tumor tissue and organs were homogenized in the cell lysis buffer using Polytron homogenizer (Westbury, N.Y., USA). Raf-1 expression was analyzed in tissue homogenates by immunoprecipitation and immunoblotting as described above.

Raf-1 Protein Kinase Activity Assay

Logarithmically growing SQ-20B cells were treated with 10 μM LE-ATG-AS raf ODN, LE-ATG-S raf ODN or blank liposomes for 8 h in 1% FBS containing medium. Cells were lysed as described above, and lysates, normalized for protein content, were immunoprecipitated with agarose-conjugated anti-Raf-1 antibody overnight at 4° C. Raf-1 phosphotransferase activity was assayed in vitro using its physiological substrate, mitogen-activated protein kinase kinase (MKK1) $^{32}$ in kinase buffer containing 30 mM Hepes (pH 7.4), 1 mM manganese chloride,1 mM DTT, 0.1 mM ATP, and 20 μCi [λ-$^{32}$P]ATP (6000 Ci/mmol) as described before.[21] Radiolabeled reaction products were separated by 10% SDS-PAGE and auto-radiographed. The MKK1 bands were quantified using the Image-Quant program (Molecular Dynamics).

Radiation Survival Dose Response Assay

The appropriate numbers of SQ-20B cells were seeded in duplicate T-25 tissue culture flasks (Corning, N.Y., USA) in medium containing 20% FBS, and allowed to attach for 8 h at 37° C. The medium was replaced with medium containing 1% FBS and the cells were exposed to 10 μM LE-ATG-AS raf ODN, 10 μM LE-ATG-S raf ODN or 10 μM blank liposomes for 6 h before irradiation. Irradiations were performed using $^{137}$Cs gamma irradiator (JL Shepard MARK I irradiator) and a dose rate of 114 cGy/min. The cells were irradiated with total doses of 1 Gy, 3 Gy, 5 Gy and 13 Gy, followed by incubation for 2 h. The medium in all flasks was then replaced with 20% FBS containing medium and incubations continued for 7–10 days. Surviving colonies were fixed and stained with 0.5% methylene blue and 0.13% carbol fuchsin in methanol. Colonies containing 50 or more cells were scored and data were fitted to the computer-generated single-hit multitarget and linear-quadratic models of radiation survival response.[44]

Experimental Results

PC/CHOL/DDAB Liposomal Formulation of raf ODN is Nontoxic

Cationic liposomes were prepared using a combination of one of the three cationic lipids (DDAB, DOTAP and DMTAP), phosphatidylcholine (PC), and cholesterol (CHOL) in a molar ratio of 1:3.2:1.5 as described in Materials and methods. Initially, we determined the ODN entrapment efficiency of liposomes by scintillation counting of an aliquot of the preparation in which traces of radiolabeled antisense (ATG-AS) or sense (ATG-S) raf ODN was added to the initial ODN, PC/CHOL/DDAB formulation yielded the maximum ODN entrapment efficiency (>90%, n=10). PC/CHOL/DOTAP and PC/CHOL/DMTAP liposomes were found to be highly cytotoxic. Therefore, the subsequent experiments were performed using the PC/CHOL/DDAB formulation of liposomes.

Fluorescence image analysis using fluorescein-labeled ATG-AS raf ODN was performed to visualize the encapsulation of ODNs in liposomes. A heterogeneous size population of liposomes was obtained including relatively large (FIG. 7) and small liposomes (<2 microns, data not shown). In general, the liposomes showed a tendency to form small aggregates, which could be easily dispersed by gentle shaking. The ODN appeared to be distributed in the lipid bilayers and aqueous spaces. We next compared the effects of blank liposomes (BL), liposome-encapsulated antisense (LE-ATG-AS) and sense (LE-ATG-S) raf ODNs on cell survival. Blank liposomes, at a concentration equivalent to 10.0 μM or less of LE-ATG-AS/S raf ODN were non-toxic as determined by the clonogenic survival and trypan blue dye exclusion methods (data not shown). However, blank liposomes showed cytotoxicity at doses higher than 20 μM and, therefore, doses of 10 μM or less were used for the subsequent in vitro studies. For in vivo studies, mice were intravenously (i.v.) treated with a daily dose of 6 mg/kg blank liposomes for 2 weeks, and then monitored for the next 30 days. No signs of weight loss or discomfort were noted, indicating that this liposomal formulation is nontoxic in vivo.

Liposomal Encapsulation Enhances raf ODN Uptake in vitro and Stability in vitro and in vivo We have previously demonstrated that <2% of the free ATG-AS raf ODN was taken up by SQ-20B cells at 6 hours when exposed to 100 μM concentration in the presence of low serum (1%), and the maximal uptake was approximately 4% at 12 hours after treatment. In the present study, we asked whether liposome encapsulation enhances the uptake and stability of ODN in tumor cells. The kinetics of cellular uptake of LE-ATG-AS raf ODN in the presence of 1% serum is shown in FIG. 8. The intracellular level of ODN increased over time, reaching a plateau 8 hours after incubation. Approximately 13% of the total applied LE-ATG-AS raf ODN (10 μM) was incorporated into the cells. These results demonstrate that a significant increase in the intracellular level of ODN was achieved when tumor cells were treated with a 10-fold lower concentration of LE-ATG-AS raf ODN as compared with free ATG-AS raf ODN.

To examine the intracellular stability of LE-ATG-AS raf ODN, $^{32}$P-labeled ODN was recovered at various times following initial treatment of cells with radiolabeled LE-ATG-AS raf ODN (10 μM) for 4 hours. The integrity of the ODN was determined by denaturing gel electrophoresis as described in Materials and methods. Intact raf ODN (15-mer) was identified and no degradation was observed up to 24 hours (FIG. 8B Igne). In contrast, cells treated with an equimolar concentration of free ATG-AS raf ODN, showed no detectable ODN at all time-points (data not shown). In other studies, 15-mer ODN was intact following incubation of LE-ATG-AS raf ODN for 24 hours in medium containing relatively high levels of serum (15% FBS) (data not shown). These results suggest that liposomal encapsulation protects raf ODN from serum nuclease-induced degradation.

The plasma pharmacokinetics of LE-ATG-AS raf ODN is shown in FIG. 3. Following i.v. administration, the peak plasma concentration of 6.39 μg/ml was achieved and intact. ODN could be detected up to 24 hours. The decrease in plasma concentration of LE-ATG-AS raf ODN followed a biexponential pattern with an initial half-life ($t_1/2_\beta$) of 24.5 minutes and a terminal half-life $t_1/2_\beta$ of 11.36 h. The area under the plasma concentration-time curve for LE-ATG-AS raf ODN was 5.99 μg.h/ml, with total body clearance of 75.94 ml/min/kg and volume of distribution of 74.67 l/kg. In contrast, intact, free ATG-AS raf ODN was detectable only at 5 min; with a plasma concentration of 9.75 μg/ml. These observations are in agreement with the in vitro observations, and suggest that free ATG-AS raf ODN is rapidly degraded in plasma, whereas LE-ATG-AS raf ODN is in circulation for up to 24 hours.

The tissue distribution of LE-ATG-AS raf ODN is shown in FIG. 4. Intact ODN was detected in all organs examined up to 48 hours (FIG. 4a). Following the administration of free ATG-AS raf ODN; intact ODN was seen only at 5 minutes in various organs and degradative products (<15-mer) were subsequently found (data not shown). Previous reports of the pharmacokinetic profiles of the fully phosphorothioated ODNs (S-oligos), delivered without a carrier, suggest that liver and kidney are the preferential sites of ODN accumulation. Our data are in agreement with these studies, however, the possibility remains that liposomal delivery may have facilitated targeting of ODN to certain tissues, including liver and kidney. The present findings suggest that raf ODNs, with only the 3' and 5' base linkages phosphorothioated, are rapidly degraded, and that liposome encapsulation is an effective approach for maintaining the ODN stability in various organs for at least 48 h.

Liposome-encapsulated ATG-AS raf ODN Inhibits Raf-a Expression and Activity in vitro The time-course experiments revealed that a maximum inhibition of Raf-1 protein expression (52.3±5.7%, approximately 74 kDa) occurred 8 hours after incubation of cells with 10 μM LE-ATG-AS raf ODN (FIG. 5a). The inhibitory effect of LE-ATG-AS raf ODN (AS) was seen up to 24 hours (45.6±9.8%). The levels of Raf-1 protein were comparable in the control untreated cells (C), blank liposome-treated cells (BL), and LE-ATG-S raf ODN-treated cells (S) (FIG. 5a), demonstrating that LE-ATG-AS raf ODN specifically inhibited the Raf-1 protein expression in SQ-20B cells. Dose-response studies showed that 35.94±16.8% and 52.3±5.7% inhibition of Raf-1 expression occurred after treatment of cells for 8 hours with 5 μM and 10 μM LE-ATG-AS raf ODN, respectively (FIG. 5b).

We examined the effect of LE-ATG-AS raf ODN on the enzymatic activity of Raf-1 protein kinase using its physiological substrate, mitogen-activated protein kinase kinase (MKK1).[32] Raf-1 protein kinase activity was comparable in control, untreated cells and LE-ATG-S raf ODN-treated cells (10 μM, 8 hours). In concurrence with the level of inhibition of Raf-1 protein expression, the in vitro phosphotransferase activity of Raf-1 protein kinase was inhibited in LE-ATG-AS raf ODN-treated cells compared with control cells (10 μM, 8 hours; 62.6±9.0%) (FIG. 6).

Liposome-encapsulated A TG-AS raf ODN Inhibits Raf-1 Expression in vivo

In Balb/c nu/nu mice, the endogenous levels of Raf-1 expression varied in different normal tissues, and the expression levels were found to be in the descending order of lung>liver>spleen>heart>kidney (data not shown). Interestingly, anti-Raf-1 antibody recognized two protein bands (approximately 74 kDa and approximately 55 kDa) only in kidneys. It is unclear whether the smaller fragment is a proteolytic product of Raf-1 in mouse kidney (FIG. 7). The mouse and human c-raf-1 cDNAs share a conserved nucleotide sequence in the translation initiation region (Leszek Woznowski, personal communication). Therefore, we examined the effect of ATG-AS/S raf ODN on Raf-1 expression in normal mouse tissues. No inhibition of Raf-1 expression was observed in normal tissues following i.v. administration of free ATG-AS raf ODN (6 mg/kg, daily for 5 days) (data not shown). However, i.v. administration of the LE-ATG-AS raf ODN (6 mg/kg, daily for 5 days), but not LE-ATG-S raf ODN, led to a significant inhibition of Raf-1 (approximately 74 kDa) in liver (51.6±17.4%; n=3), and kidneys (42.2±11.0%; n=3) (FIG. 7). LE-ATG-AS raf ODN-associated inhibition of Raf-1 did not occur in heart and lungs (n=3, data not shown). These observations are consistent with the normal tissue disposition profiles of LE-ATG-AS raf ODN, showing a relatively higher accumulation of ODN in liver and kidneys compared with heart and lungs (FIG. 4b). It remains to be seen whether inhibition of Raf-1 in liver and kidney is associated with any appreciable toxicities to these organs.

Surprisingly, i.v. treatment with LE-ATG-AS raf ODN resulted in variable effects on Raf-1 expression in different SQ-208 tumor xenografts, with levels of inhibition ranging from 37.6 to 57.6% compared with LE-ATG-S rafODN-treated tumor xenografts (n=3) (FIG. 7). We interpret this to be due to differences in tumor vasculature in different xenografts, impeding the delivery of ODN to poorly perfused tumor sites. Intravenous treatment with free ATG-AS/S raf ODN, LE-ATG-S raf ODN (S), bland liposomes, or normal saline (C) had no effect on Raf-1 expression in tumor tissue compared with untreated controls. Variations in the level of Raf-1 inhibition observed after i.v. treatment prompted us to investigate the effect of intratumoral administration of LE-ATG-AS raf ODN or LE-ATG-S raf ODN on Raf-1 expression. Results shown in FIG. 8 demonstrate a significant inhibition of Raf-1 protein expression in SQ-20B tumor xenografts following intratumoral treatment with LE-ATF-AS raf ODN compared with LE-ATG-S raf ODN (60.3±5.4%; 11-3). Taken together, these data demonstrate that LE-ATG-AS raf ODN inhibits Raf-1 expression in a sequence-specific manner in vivo.

SQ-20B cells treated with liposome-encapsulated ATG-AS raf ODN are radiosensitive. Radiation survival dose responses of SQ-20B cells exposed to LE-ATG-AS raf ODN, LE-ATG-S raf ODN, or blank liposomes are presented in Table 1. The plating efficiencies of cells treated with LE-ATG-S/AS rafODN or blank liposomes were comparable (Table 1). The single-hit, multitarget (target model) and the linear quadratic model (LQ) are most commonly used to analyze cellular radiation survival. The target model is based on the parameters $D_0$ and fl, where $D_0$ is the inverse of the terminal slope of the survival curve and fl is the extrapolation of this slope to the ordinate. The higher the $D_0$ value, the more resistant are cells to radiation-induced cell killing. Another parameter, $D_q$ is the measure of the shoulder of the survival curve as the terminal slope line intersects the abscissa. The LQ model has two major parameters: α, the linear component characterizing the radiation response at lower doses; and β, the quadratic component characterizing the response at higher doses. The higher the value of α, the more sensitive are the cells to radiation. A model-free parameter, D is called the mean inactivation dose and represents the area under the survival curve plotted on linear coordinates. Clonogenic cell survival data were computer-fitted to the single hit multitarget and the linear-quadratic models of radiation survival response. Significant decreases observed in the values of radiobiological parameters, D, $D_0$, and $D_0$ of SQ-20B cells following treatment with LE-ATG-AS rafODN suggest a good correlation between the antisense sequence-specific inhibition of Raf-1 protein kinase and radiosensitization. Based on a ratio of the mean inactivation dose, the dose modifying factor (DMF) of LE-ATG-AS raf ODN treatment (10 μm) was approximately 1.6. These data are significant because a 10-fold higher concentration of the free ATG-AS raf ODN is required to achieve a comparable level of the radiosensitization of SQ-20B cells (ATG-AS raf ODN, 100 μm; DMF approximately 1.4).

TABLE 1

Radiation survival parameters of SQ-20B cells treated with LE-ATG-S/AS raf ODN

| raf ODN | No. of experiments | $D_0$ (Gy) | $D_4$ (Gy) | η | α ($Gy^{mi}$) | β ($Gy^2$) | D (Gy) |
|---|---|---|---|---|---|---|---|
| Blank liposomes/ LE-ATG-S- | 5 | 2.795 ± 0.38 | 1.445 ± 1.22 | 2.012 ± 1.34 | 0.2184 ± 0.11 | 0.0087 ± 0.00 | 3.659 ± 0.02 |
| LE-ATG-AS | 3 | 2.287 ± 0.23 | 0.051 ± 0.05 | 1.021 ± 0.19 | 0.4385 ± 0.05 | 0.0000 ± 0.00 | 2.280 ± 0.00 |

The appropriate number of cells were seeded in duplicate T-25 flasks per dose in each experiment as explained in Materials and method. Plating efficiencies of the blank liposome treated, LE-ATG s raf ODN-treated and LE-ATG-AS raf ODN-treated cells were in the range of 65–79%, 52–83% and 59–90% respectively.
Composite value of the various parameters were obtained from the three experiments performed with LE-ATG raf ODN-treated cells and two experiments performed with the blank liposome-treated cells.

ANALYSIS

The above results indicated that a cationic liposome formulation according to the invention (PC/CHOL/DDAB) has several advantages. Specifically, the PC/CHOL/DDAB liposomal formulation was found to be nontoxic, and yielded a high ODN encapsulation efficiency.

We have identified several in vivo parameters which indicate that these cationic liposomes are a suitable vehicle to transport antisense oligos safely and effectively. Based on fluorescence microscopy, it appears that oligos may be entrapped inside the lipid bilayer (FIG. 1). The observations extend the initial reports that showed encapsulation of plasmid DNA within lipid sheets or tubes. By simultaneously measuring plasma and tissue levels, we also demonstrate that liposomal encapsulation of oligos protects these relatively small pieces of DNA from degradation in plasma and facilitates their tissue accumulation (FIGS. 3 and 4). Circulating antisense raf oligos carried in vivo by liposomes were intact for at least 24 hours, while free oligos were undetectable after five minutes. These data are in agreement with previous reports showing that phosphodiester oligos with only two terminal phosphorothioate linkages at the 3' and 5' ends resemble the unblocked phosphodiester oligos, and that these oligos are rapidly cleared from the blood and show little tissue accumulation. It is hypothesized that the use of PC along with cholesterol in our liposomal preparation may have facilitated the prolonged retention of oligos in the circulation, as well as tissue disposition and stability of oligos.

Particle size has been shown to play a major role in liposome biodistribution and the route of cell entry. Larger liposomes are distributed primarily to the reticuloendothelial system with negligible amounts in other tissues, whereas smaller liposomes are localized to other organs. Additionally, the clearance of multilamellar vesicles of heterogenous size distribution follows a biphasic pattern, with rapid clearance of larger liposomes and a slow rate of clearance of small liposomes. Limited information is available on the biodistribution of cationic liposomes containing oligonucleotides. Litzinger and colleagues previously reported that oligonucleotides complexed with cationic liposomes, approximately 2.0 microns in diameter, are transiently taken up by the lungs followed by rapid distribution to liver. Recent studies demonstrated that endocytosis is the principal pathway for delivery of oligonucleotides via cationic liposomes. Our liposomal preparations consisted of both large and small liposomes. Consistent with the above notion, we demonstrate that the clearance of LE-ATG-AS raf ODN followed a biphasic pattern with preferential distribution to liver.

Liposome-encapsulated antisense raf oligos were nontoxic, and inhibited Raf-1 expression in vitro and in vivo in a sequence-specific manner (FIGS. 5–8 and Table 1). It is noteworthy that intravenous and intratumoral routes of LE-ATG-AS raf ODN administration led to a significant inhibition of Raf-1 expression in SQ-20B tumor tissue, suggesting the potential applicability of this compound for both systemic and local administrations. Furthermore, tumor cells treated with liposomal-encapsulated antisense raf oligo were radiosensitive compared with control cells (Table 1). More recently, in collaboration with Dr. Brett Monia (ISIS Pharmaceuticals, Carlsbad, Calif., USA), experiments have been initiated to demonstrate the radiosensitizing effect of liposome-encapsulated antisense raf oligo (5132) in the SQ-20B tumor xenograft model. The in vivo data obtained so far in athymic mice are promising (Gokhale et al. unpublished data). The present results suggest that liposomal delivery of ATG-AS raf ODN in combination with radiation may be an effective gene-targeting approach for treatment of cancers, especially those that are resistant to standard radiation therapy.

EXAMPLE 2

Materials and Methods

Cell Culture

SQ-20B tumor cells were grown as a monolayer in Dulbecco's modified Eagle's medium (DMEM) (GIBCO BRL, Grand Island, N.Y.) supplemented with 20% heat-inactivated fetal bovine serum (FBS), 2 mM glutamine, 0.1 mM nonessential amino acids, 0.4µg/ml hydrocortisone, 100 µg/ml streptomycin, and 100 U/ml penicillin.

Oligodeoxyribonucleotides

A 20-mer phosphorothioate antisense ODN (ISIS 5132/5132: 5'-TCC-CGC-CTG-TGA-CAT-GCA-TT-3') corresponding to the 3'-untranslated region (3'-UTR) of human c-raf-1 mRNA and a seven-base mismatched phosphorothioate antisense ODN (ISIS 10353/10353; 5'-TCC-CGC-GCA-CTT-GAT-GCA-TT-3') were designed and synthesized as described previously (Monia et al., 1996a,b). A 20-mer phosphorothioate sense ODN (5'-ATT-GCA-TGT-CAC-AGG-CGG-GA-3') was synthesized at Lofstrand Labs Limited (Gaithersburg, Md.) as described previously (Soldatenkov et al., 1997).

Preparation of Cationic Liposomes

ODN was encapsulated in cationic liposomes prepared using dimethyldioctadecyl ammonium bromide, phosphatidylcholine, and cholesterol (Avanti Polar Lipids, Alabaster, Ala.) in a molar ratio of 1:3,2:1,6 as described in previously (Gokhale et al., 1997). Briefly, the lipids dissolved in chloroform or methanol were evaporated to dryness in a round-bottomed flask using a rotary vacuum evaporator. The dried lipid film was hydrated overnight at 4° C. by adding 5132/10353 at 1.0 mg/ml in phosphate-buffered saline (PBS). The film was dispersed by vigorous vortexing, and the liposome suspension was sonicated for 5 minutes in a bath-type sonicator (Laboratory Supplies, Hicksville, N.Y.). The ODN/lipid ratio was 30 µg ODN/mg lipid, resulting in greater than 90% encapsulation efficiency. The liposome-encapsulated ODN (LE-5132/LE-10353) was stored at 4° C. and used within a week. Blank liposomes (BL) were prepared exactly as described in the absence of ODN.

Raf-1 Immunoprecipitation and Immunoblotting Assays

For in vitro expression studies, on day 1, logarithmically growing SQ-20B cells were exposed to various concentrations of LE-5132, 5132, LE-10353, or BL in 1% FBS-containing medium for 6 hours. The cells were then washed with 20% FBS containing medium to remove liposomes, and incubation in 20% FBS-containing medium continued overnight (18 hours) in the presence of 5132 in the LE-5132 and 5132 treatment groups and the presence of 10353 in the LE-10353 group. On day two, cells were rinsed with fresh 30% FBS, followed by a second course of the treatment schedule as on day one for an additional 24 hours. This procedure yielded a minimal exposure of cells of LE-5132 (12 hours). Cells were then lysed in the buffer containing 500 mM HEPES, ph 7.2 1% NP-40, 10% glycerol, 5 mM sodium orthovanadate, 1 mM phenylmethysulfonyl fluoride, 20 µg/ml aprotinin, and 20 µg/ml leupeptin. The lysates were clarified by centrifugation at 16,000 g for 20 minutes, and the protein concentrations were determined (Pierce, Rockford, Ill.). Whole cell lysates, normalized for protein content, were used for immunoprecipitation of Raf-1, using protein A-agarose-conjugated rabbit polyclonal antibody against 12 carboxy-terminal amino acids of human Raf-1 p74 (Santa Cruz Biotechnology, Santa Cruz, Calif.). The immunoprecipitates were sequentially washed with cell lysis buffer, 0.5 M LiCl, 100 mM Tris-HCl, pH 7.4, and 10 mM Tris-HCl, pH 7.4. The immune complexes were boiled in Laemmli sample buffer and resolved by 7.5% SDS-PAGE. This was followed by immunoblotting with polyclonal anti-Raf-1 antibody and detection of Raf-1 using ECL reagents according to the manufacturer's protocol (Amersham Corporation, Arlington Heights, Ill.). The Raf-1 protein level was quantified using the computer software program Image-Quant (Molecular Dynamics, Sunnyvale, Calif.).

For in vivo expression studies, tumor tissue was homogenized in the cell lysis buffer using a Polytron homogenizer (Westbury, N.Y.). Raf-1 expression was analyzed in tissue homogenates by immunoprecipitation and immunoblotting as described above.

In vitro Coagulation Assay

The coagulation, assay was performed using normal human plasma containing a known concentration of LE-5132 or 5132. The activated partial thromboplastin time (APTT) was measured after adding APTT reagent (rabbit brain cephalin extract with ollagic acid activator) (Sigma Diagnostics, St. Louis, Mo.) to plasma samples, followed by addition of calcium chloride to initiate clot formation according to the manufacturer's recommendations (Sigma Diagnostics). The time required to form visible clots was recorded manually.

Pharmacokinetic Studies

Male Balb/c nu/nu mice (National Cancer Institute, Frederick, Md.) were maintained in the Division of Comparative Medicine, Georgetown University, according to accredited procedures, and fed purina chow and water ad libitum. Mice were injected i.v. via the tail vein with 30 mg/kg of LE-5132 or 5132 formulated in PBS. At 5, 15, and 30 minutes and 1, 2, 4, 8, 24, and 48 hours after injection, animals were bled, under anesthesia, from the retroorbital sinus into heparinized tubes and killed by cervical dislocation. The blood was centrifuged immediately at 300g for 10 minutes at 4° C. to separate the plasma. The liver, spleen, kidney, heart, and lungs were rapidly excised and rinsed in ice-cold normal saline. The plasma and organs were stored at −70° C. until further analysis.

Antisense raf ODN concentrations in plasma and tissue samples were detected as we described earlier (Gokhale et al., 1997). Briefly, the ODN was isolated from plasma samples using the phenol-chloroform extraction method and from tissues using a DNA extraction kit (Stratagene, La Jolla, Calif.). The raf ODN concentration standards were prepared by adding known amounts of 5132 in blank plasma or blank tissue samples, followed by extraction as described earlier. The extracts were loaded onto 20% polyacrylamide/8 M urea gels and electrophoresed in TBE buffer. The gels were electroblotted onto nylon membranes in 0.5×TBE buffer at 20 V for one hour, and the blots were probed with [$^{32}$P]-labeled sense raf ODN probe in Quickhyb buffer (Stratagene) at 30° C. overnight. A 10–50-fold excess of the probe was used to ensure saturation of all bands. The autoradiographs were scanned using a computer program (Image-Quant software), and the amounts of antisense raf ODN in the samples were calculated by comparison with standards.

In vivo LE-5132 Treatment and Irradiation Procedures: Antitumor Efficacy Study Design Logarithmically growing SQ-20B cells were injected s.c. (2×10$^6$ cells) in the left flank region in male Balb/c nu/nu mice under mild anesthesia. Tumors were allowed to grow to a mean tumor volume of ~72–94 mm$^3$ before initiation of treatment. Volumes for tumors were determined from caliper measurements of the three major axes (a,b,c) and calculated using abc/2, an approximation for the volume of an ellipse ($\pi abc/6$).

For each experiment, tumor-bearing mice were randomly divided into different treatment group, with 5–7 animals per group. The ODN group of mice received LE-5 132 i.v. at a dose of 6–10 mg/kg daily or on alternate days for a total of 12–18 days or by both methods. The tumors in the IR group were irradiated using a [$^{137}$Cs] irradiator (J. J. Shepard Mark I). Animal restraint and shielding of normal tissues were accomplished within a hinged hemicylindrical plastic chamber mounted behind a specially shaped 2.5 cm thick lead shield. The tumor-bearing hind limb protruded through a hole in the chamber and was mounted, by taping the foot, on a 1.6 mm Plexiglas platform exposed to the irradiation. Using TLD dosimetry, the average dose rate to the center of the tumor and to the mouse body were determined beforehand using the experimental irradiation conditions and a custom-made, tissue-equivalent, mouse phantom. Dose distributions were confirmed on several mice. Radiation was delivered to the tumors at a dose rate of 2.37 Gy/min. for 3.8 Gy daily for up to 18 days. The whole body dose was <5% of the tumor dose (0.19 Gy/day). No gastrointestinal problems were noted for the duration of the experiment in any mice. The combined treatment group of animals received LE-5 132 on day 0 and LE-5132 and IR at an interval of 3–4 hours on days 1–6, and on days 8, 10, and 12. In addition, this group received IR alone on days 7, 9, and 1I1 and days 13–18. Of the two control groups, one received BL on the same dosing schedule as LE-3132 (BL) and the other was left untreated (C). Tumor volumes were monitored once or twice weekly and for 12–27 days after the final treatment.

Tumor volumes were calculated as the percentage of initial tumor volume (day 0, the first day of dosing), and mean tumor volume±SE was plotted. Analysis of variance (one-way ANOVA) was performed to determine the statistical significance of changes in tumor volumes observed on day 12 after the final treatment.

Histopathology

Tumor tissues were excised from representative treatment groups 24 hours after the last treatment and fixed in 10% formalin, and paraffin sections were analyzed microscopically after hematoxylin/cosin staining. Histologic changes, such as apoptotic cells containing fragmented chromatin, were scored under the light microscope (American Optical Corporation, Buffalo, N.Y.). Ten fields with approximately 100 cells per field were scored in each treatment group.

Experimental Results

LE-5132 Inhibits Raf-1 Expression in vitro

To establish the antisense ODN sequence-specific inhibition of Raf-1 expression, SQ-20B tumor cells were treated with 5132, LE-5132, and a seven base mismatch LE-10353 (FIG. 9A). Previously, in vitro inhibition of Raf-1 with 5132 has been shown to require lipofectin (Monia et al., 1996a). Consistently, 5132 was found to be ineffective in cell culture (FIG. 9A, lanes 4 and 6). A significant decline in the level of Raf-1 protein was observed with LE-5132 compared with 5132 treatment in vitro (FIG. 9B, 0.5 µM LE-5132 LE-5132, 71.3±22.5%; 1.0 µM LE-5132, 79.6±16.7%). Liposome-encapsulated mismatch antisense ODN (LE- 10353) showed Raf-1 expression comparable to untreated or BL-treated cells (FIG. 9A, lanes 7–9). Taken together, these data establish the antisense sequence specific potency of LE-5132 in SQ-20B cells.

LE-5132 Does not Affect Coagulation in vitro

As a step toward the clinical application of cationic liposomes to deliver ODN safely and effectively, we compared the effects of 5132 and LE-5132 on coagulation time, using normal human plasma. Addition of 5132 to normal human plasma produced concentration-dependent prolongation of clotting time (FIG. 10). Approximately 95% and 197.5% increases in APTT were observed in vitro in the presence of 100 µg/ml and 200 µg/ml of 5132, respectively, whereas only marginal increases in APTT were seen with LE-5132 (100 µg/ml, 13%; 200 µg/l, 14.5%). BL in the same concentration range showed no effect on APTT (data not shown).

Liposome-encapsulation Enhances Pharmacokinetics of 5132

The pharmacokinetic parameters were obtained after a single i.v. bolus administration of LE-5132 or 5132. As shown in FIG. 11A and B, intact ODN could be detected in plasma for at least up to 8 hours in both cases. The peak plasma concentrations at 5 minutes after ODN administrations were 28.5 µg/ml and 13.5 µg/ml for LE-5132 and 5132, respectively. The decrease in plasma concentration of LE-5132 and 5132 followed a biexponential pattern with initial distribution half-life ($t_1/2_\beta$) of 34. minutes and 21.6 minutes, respectively. The terminal half-lives ($t_1/2_\beta$) with LE-5132 and 5132 were 14.5 hours and 4.3 hours, respectively. As shown in Table 2, the area under the plasma concentration-time curve (AUC) was 5.8 times higher with LE-5132 compared with 5132, and the rate of clearance of intact ODN was higher with 5132 compared with LE-5132.

The normal tissue distribution profiles of LE-5132 and 5132 are presented as a function of the AUC in FIG. 12. Following either treatment, intact ODN could be detected up to 48 hours in the organs examined (data not shown). However, the tissue distribution of LE-5132 was different from that of free phosphorothioated ODN, 5132. Significantly higher levels of intact ODN could be measured in liver (18.4-fold) and spleen (31-fold) after LE-5132 administration compared with 5132 administration. Slightly higher ODN levels were noticed in other organs via liposomal delivery of ODN compared with free ODN (heart, 3-fold; lungs, 1.5-fold). Interestingly, the level of intact ODN in kidneys was lower with LE-5132 (0.77-fold). Additional studies performed indicated a modestly higher ODN level in SQ-20B tumor tissue following LE-5132 treatment compared with 5132 treatment (1.4-fold).

LE-5132 Inhibits SQ-20B Tumor Growth

As shown in FIG. 13, antitumor effects of LE-5132 were observed within a week after treatment initiation, and mean tumor volume continued to decrease during the course of subsequent treatments. On the final day of treatment (day 19), mean tumor volumes were 42.0±5.5% and 290.6%±26.6% of initial volume (day 0, 100%) in the LE-5132 and BL groups, respectively. The tumor volume in the LE-5132 group reached the initial volume within 6–10 days after the last dosing. A remarkable difference in the tumor volumes was noticed in the LE-5132 and BL groups at all times after treatment. The study was terminated on day 30, at which time the mean tumor volume in the BL group was approximately 3.4-fold more than that of the LE-5132 group.

In other studies, we compared the antitumor efficacies of LE-5132 and 5132. LE-5132 or 5132 (10 mg/kg) was administered i.v. into tumor-bearing mice daily for the first 7 days, followed by three additional doses on alternate days. The control group received similar treatment with BL or was not treated at all (C). Tumor volumes were monitored for a total of 35 days. Mean tumor volumes on day 35 compared with day 0 (100%) were: BL, 427.8%±32.5%; C, 405.3%±26.8%; 5132, 159.6±% 10.0%; LE-5132, 105.3%±1 6.3%. ANOVA was performed to determine the significance of difference in mean tumor volumes in various categories on day 35. Tumor growth patterns were comparable in the BL and C control groups. Both the 5132 and LE-5132 groups displayed significant antitumor activity vs. the BL and C groups (n=5, p<0.0001). However, the LE-5132 group displayed greater antitumor activity relative to 5132 (n=5, p<0.001). These data are consistent with relatively increased plasma, normal tissue, and tumor levels of 5132 in the liposome-encapsulated form.

LE-5132 Inhibits Raf-1 Expression in vivo

Relative Raf-1 protein levels were measured in SQ-20B tumor tissue in mice exposed to LE-5132±IR or BL (FIG. 14).

TABLE 2

EFFECT OF LIPOSOME ENCAPSULATION
ON PHARMACOKINETIC PARAMETERS OF ODN[a]

| ODN | $t_1/2_\beta$[b] (hours) | $C_{max}$ (µg/ml) | $AUC_{area}$ (µg·h/ml) | CL (L/h/kg) | $Vd_{area}$ (L/kg) |
|---|---|---|---|---|---|
| 5132 | 4.30 | 13.57 | 6.20 | 4.82 | 29.96 |
| LE-5132 | 14.50 | 28.50 | 36.60 | 0.82 | 17.15 |

[a]30 mg/kg bolus, i.v. in Balb/c nu/nu mice.
[b]$t_1/2_\beta$, elimination half-life; $C_{max}$ peak plasma concentration;
AUC, area under the plasma concentration-time curve; CL, total body clearance; $V_{area}$, volume of distribution.

In the LE-5132 group, Raf-1 expression was found to be 35.5%±13.4% and 27.7%±13.3% compared with the BL group (100%) on day 7 and day 14, respectively. Inhibition of Raf-1 expression was also noted in SQ-20B tumors in mice treated with a combination of LE-5132 and IR. IR treatment alone did not change Raf-1 expression compared with the untreated or BL control (FIG. 14).

LE=5132 is a Tumor Radiosensitizer

Because SQ-20B cells were established from a tumor after failure of radiation therapy and LE-5132 treatment caused tumor growth arrest during the course of treatment, we asked if control of growth of this relatively radioresistant tumor could be achieved by a combination of LE-5132 and IR treatments. LE-5132 (10 mg/kg) was administered ten times over 12 days (day 0-day 12). This treatment caused tumor growth arrest compared with control groups of mice (untreated and BL) for up to one week after the last dosing (day 19). This was followed by a steady increase in tumor volume (FIG. 15A). IR (3.8 Gy/day) was given daily for eighteen days. In this group, a modest decline in mean tumor volume was observed by day 26 (14.9%±7.1 % of initial volume) (FIG. 7A). Tumors grew thereafter and reached the initial volume within the next in 3–7 days. The combination of LE-5132 and IR treatment caused a significant decrease in the mean tumor volume by day 26 (57.9%±8.0% of initial volume). By day thirty, the mean tumor volumes compared with initial volumes (100%, day 0) were: LE-5132, 122.5%±13.8%; IR, 113.8%±17.6%; LE-5132+IR, 43.5%±2.9%; LB/untreated control, 370.8%±15.6% (FIG. 15). Both LE-5132 and IR groups displayed significant tumor growth arrest vs. BL and untreated groups (p<0.001). Statistical analysis indicated that tumor volume difference was insignificant in the IR vs. the LE-5132 group. Most important, the LE-5132+IR group displayed significantly greater antitumor activity vs. LE-5132, IR, BL, and untreated groups (p<0.001) (FIG. 15B).

Figure 16:
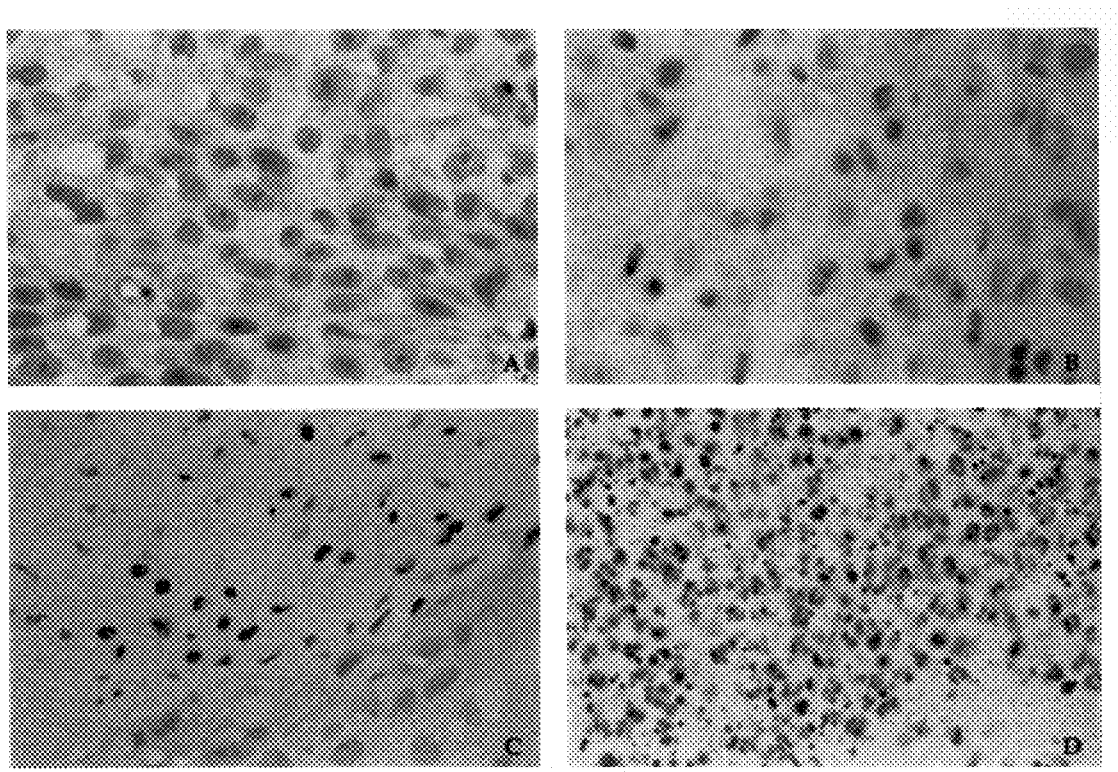

Combination of LE-5132 and IR Treatments Causes Significant Increase in Apoptosis in vivo Representative tumors in various treatment groups were excised 24 hours after the last treatment for histopathologic examination. Both necrotic and apoptotic cells were seen in the LE-5132 or IR group compared with the untreated group. In addition, clonal regrowth of some viable cells containing intact nuclei was observed in the IR group (data not shown). The proportion of apoptotic cells containing highly fragmented nuclei was considerable higher in the LE-5132+IR group compared with the single agent or untreated control group (FIG. 16). The ratios of the relative number of apoptotic cells/viable cells scored in different groups were: C, 0.06 LE-5132, 0.64; IR, 0.72; LE-5132+IR, 2.46.

Discussion

Antisense ODN therapeutics is a novel approach to enhance the efficacy of an anticancer agent via sequence-specific inhibition of a proliferative or survival signal. To our knowledge, this report provides the first evidence of the effectiveness of a well-characterized antisense ODN as a radiosensitizer in an animal tumor model. SQ-20B tumor cells were established from a laryngeal squamous cell carcinoma of a patient who had failed a full course of radiation therapy. Radiation or antisense raf ODN treatment alone caused temporary inhibition of SQ-20B tumor growth but not tumor regression, whereas a combination of antisense raf ODN and radiation treatments led to sustained tumor regression for at least 27 days after treatment (FIGS. 13 and 15). These data support the role of Raf-1 in cell proliferation and survival and establish antisense rad ODN as a novel in vivo radiosensitizer.

We found significant inhibition of Raf-1 protein expression following LE-5132 treatment of SQ-20B cells and tumor, suggesting that LE-5 132 is a biologically active compound in vitro and in vivo (FIGS. 9 and 14). Because the 5132 sequence corresponds to a 3' UTR of human c-raf-1 not conserved in mouse, inhibition of Raf-1 in normal mouse tissues could not be investigated. Previous studies have indicated that among other potentially toxic effects, PS-ODN treatment causes bruising associated with dose-dependent prolongation of the clotting time. Complement and coagulation effects of PS-ODN including 5132 could be avoided by altering the dosing regimen. Our results show that liposomal encapsulation of 5132 (LE-5132) prevents changes in coagulation time (FIG. 10). Also, liposomal delivery of ODN may alleviate many of the other sequence-independent side effects of PS-ODN, including hematologic changes and complement activation. Significant elevation in plasma concentration and most tissue levels of the liposomal formulation of 5132 was observed compared with free 5132 (FIGS. 11 and 12 and Table 2). Consistent with this, anti-tumor potency of LE-5132 was found to be significantly higher than that of 5132. Taken together, these data suggest that liposome encapsulation is an efficacious method of ODN transport in vivo.

The mechanism by which inhibition of Raf-1 expression enhances IR-induced cytotoxicity is not clear. The role of Raf-1 as an antiapoptotic or survival factor has been demonstrated in growth factor-deprived hematopoietic cells and in v-abl-transformed NIH/3T3 cells (Troppmair et al., 1992; Wang et al., 1996, Weissinger et al., 1997). Several reports indicate that a balance between cell death and cell survival signals determines the fate of the cells exposed to genotoxic or nongenotoxic stress. IR has been shown to activate diverse types of signaling molecules, including Raf-1 protein kinase, mitogen-activated protein kinase (MAPK), and transcription factors AP-1 and NK-κB (reviewed in Kasid and Suy, 1998). One possibility is that Raf-1 may have a protective role in irradiated cells. We have observed increased level of Bax protein, a proapoptotic member of the Bcl-2 family, in SQ-20B cells treated with either IR or a combination of LE-5132 and IR (data not shown). Radiation-inducible Bax expression has been correlated with apoptosis (Zhan et al., 1994). Furthermore, histopathologic examination revealed a significant proportion of tumor cells containing fragmented chromatin, indicative of apoptosis in the LE-5132+IR treatment group compared with the LE-5 132, IR, or untreated control groups (FIG. 16). Those data suggest that Raf-1 may serve to promote the antiapoptotic signaling pathway(s) in irradiated cells. Inhibition of Raf-1 with antisense raf ODN would then result in the substantial effects of IR-responsive proapoptotic signals, including reversal of tumor radioresistance.

EXAMPLE 3

Materials and Methods

Preparation of DMTAP:PC:CHOL Liposomes

Liposomes having a molar ratio of 1,2-dimyristoyl-3-trimethyl ammonium propane (DMTAP): phosphatidylcholine (PC): and cholesterol (CHOL), of 1:3.2:1.6, and having encapsulated therein an antitumor raf oligonucleotide (ATG-AS) were prepared using substantially the same methods described previously.

In Vitro Results

A) Enhanced Cellular Uptake of Antisense raf Oligodeoxyribonucleotides Encapsulated in Liposomes Comprised of DMTAP:PC:CHOL Dose-response Uptake Experiments SQ-20B Tumor cells were incubated with a mixture of radiolabeled ($^{32}$P-γATP) and an indicated dose of unlabeled antisense raf oligonucleotide (ATG-AS) either in the liposome encapsulated form (LE-ATG-AS) or free form (ATG-AS) (FIG. 17). The treatment lasted for 4 hours at 37° C. in 1% serum containing medium. Following incubation, cells were washed with phosphate buffered saline (PBS), detached by trypsinization, and collected by centrifugation. The cell pellet was washed twice with PBS, and cells were then lysed in 1% sodium dodecyl sulphate. The intracellular radioactivity indicative of the amount of ATG-AS taken up by the cells was determined by liquid scintillation counting. Data shown in FIG. 17 indicate a significant increase in the intracellular uptake of LE-ATG-AS at all doses tested compared to ATG-AS (1, 2, 4, 8 and 10 μM).

Time-course Uptake Experiments

SQ-20B tumor cells were incubated with a mixture of radiolabeled ($^{32}$P-γATP) and 4 μM of unlabeled antisense raf oligonucleotide (ATG-AS) either in the liposome encapsulated form (LE-ATG-AS) or free form (ATG-AS). The treatment lasted for indicated times at 37° C. in 1% serum containing medium (FIG. 18). Following incubation, cells were washed with phosphate buffered saline (PBS), detached by trypsinization, and collected by centrifugation. The cell pellet was washed twice with PBS, and cells were then lysed in 1% sodium dodecyl sulphate. The intracellular radioactivity indicative of the amount of ATG-AS taken up by the cells was determined by liquid scintillation counting. Data shown in FIG. 18 indicate a significant increase in the intracellular accumulation of LE-ATG-AS at all time points tested compared to ATG-AS (15 minutes, 30 minutes, 1 hour, 2 hours, 4 hours, 6 hours, 16 hours, and 24 hours).

B. Intracellular Stability of Antisense raf Oligodeoxyribonucleotides Encapsulated in Liposomes Comprised of DMTAP:PC:CHOL Stability Experiments SQ-20B tumor cells were incubated with a mixture of radiolabeled ($^{32}$P-γATP) and 10 μM of unlabeled antisense raf oligonucleotide (ATG-AS) either in the liposome encapsulated form (LE-ATG-AS) (FIG. 19, Lane 1) or free form (ATG-AS) (FIG. 19, lane 2). The treatment lasted for 4 hours at 37° C. in 1% serum containing medium. Immediately following incubation, cells were washed with phosphate buffered saline (PBS), detached by trypsinization, and collected by centrifugation. The cell pellet was washed twice with PBS, and cells were then lysed in 10 mM Tris-HCl, 200 mM NaCl, 1% SDS, 200 μg/ml proteinase K, pH 7.4 for 2 hours at 37° C. Oligos were extracted with phenol:chloroform, and aqueous fraction was collected. The samples were normalized for equal radioactivity, and analyzed by denaturing gel electrophoresis (15% polyacrylamide/7 M urea), followed by autoradiography. Data shown in FIG. 19 indicate intact ATG-AS oligonucleotide in cells treated with LE-ATG-AS (Lane 1), and degraded form of this oligo in cells treated with ATG-AS (Lane 2). Radiolabeled control ATG-AS standard is shown in Lane 3. These data suggest that encapsulation in the DMTAP:PC:CHOL liposome formulation inhibits degradation of oligos.

Stability Experiments

SQ-20B tumor cells were incubated with a mixture of radiolabeled ($^{32}$P-γATP) and 10 μM of unlabeled antisense raf oligonucleotide (ATG-AS) in the liposome encapsulated form (LE-ATG-AS). The treatment lasted for 4 hr at 37° C. in 1% serum containing medium. Following incubation, cells were washed with phosphate buffered saline (PBS), and incubation continued for an additional 1 hour in 20% serum containing medium. Cells were detached by trypsinization, and collected by centrifugation. The cell pellet was washed twice with PBS, and cells were then lysed in 10 mM Tris-HCl, 200 mM NaCl, 1% SDS, 200 μg/ml proteinase K, pH 7.4 for 2 hours at 37° C. Oligos were extracted with phenol:chloroform, and aqueous fraction was collected. The samples were normalized for equal radioactivity, and analyzed by denaturing gel electrophoresis (15% polyacrylamide/7 M urea), followed by autoradiography. Data shown in FIG. 20 indicate intact ATG-AS oligonucleotide in cells treated with LE-ATG-AS (Lane 1). Radiolabeled control ATG-AS standard is shown in Lane 2. These data further suggest that oligonucleotide encapsulation in the DMTAP:PC:CHOL liposome formulation protects oligos and enhances intracellular availability of intact oligos.

In Vivo Results

A. In vivo Data

Safety Studies of Liposomes Comprised of DMTAP:PC: CHOL in CD2F1 Mice

To determine the safety of cationic liposomes comprised of DMTAP:PC:CHOL, these liposomes were injected intravenously into male CD2F1 mice (n=5, total lipids equivalent to 5 mg/kg, 15 mg/kg, 25 mg/kg, and 25 mg/kg oligo conc), on day 0, 1, 3, 4, 6, 7, 9, 10, 12, 13, 15, and 16. Two the five animals were sacrificed on day 18 for pathology, and the remainder of the animals were sacrificed on day-31. Group body weights were monitored throughout the study. As shown in FIG. 21, all animals survived the treatment and showed weight gain prior to the scheduled termination of this study.

Safety of Antisense raf Oligodeoxyribonucleotides Encapsulated in Liposomes Comprised of DMTAP:PC:CHOL To determine the safety of cationic liposomes comprised of DMTAP:PC:CHOL and encapsulating antisense raf oligos (LE-ATG-AS), the liposomes containing antisense raf oligos were injected intravenously into male CD2F1 mice (n=5, 5 mg/kg, 15 mg/kg, 25 mg/kg, and 35 mg/kg oligo con), on day 0, 1, 3, 4, 6, 7, 9, 10, 12, 13, 15, and 16. Two of the five animals were sacrificed on day 18 for pathological examination, and the remainder of the animals were sacrificed on day-31. Group body weights were monitored throughout the study. As shown in FIG. 22, all animals survived the treatment and showed weight gain. These data indicate that LE-ATG-AS composition comprised of DMTAP, PC, CHOL and having encapsulated therein an antisense raf oligodeoxyribonucleotide is safe.

What is claimed is:

1. A method of radiosensitizing raf oncogene expressing tumor tissue in a subject in need of such treatment comprising administering a radiosensitizing effective amount of a cationic liposomal formulation comprising at least one cationic lipid selected from the group consisting of dimethyldioctadecyl ammonium bromide (DDAB); 1,2-dioleoyl-3-trimethyl ammonium propane (DOTAP), N-(2,3-(dioleoyloxy)propyl)-N,N,N-trimethyl ammonium chloride; 1-[2-(9(Z)-octadecenoyloxy)-ethyl]-2-(8(Z)heptadecenyl)-3-(2-hydroxyethyl)-imidazolinium chloride); and 1,2-dimyristoyl-3-trimethyl ammonium propane (DMTAP); and further comprising phosphatidylcholine and cholesterol; and further having encapsulated therein at least one antisense oligonucleotide that is at most 40 bases which specifically binds to a Raf-1 nucleic acid sequence expressed by said tumor tissue.

2. The method of claim 1, wherein the oligonucleotide ranges in size from 15 to 40 nucleotides.

3. The method of claim 1, wherein the oligonucleotide ranges in size from 15 to 25 nucleotides.

4. The method of claim 1, wherein the respective molar amounts of cationic lipid:phosphatidylcholine:cholesterol range from (1.0–2.0):(2.0–4.0):(1.0–2.0).

5. The method of claim 4, wherein said respective molar amounts are 1.0:3.2:1.6.

6. The method of claim 1, wherein the cationic lipid is DOTAP.

7. The method of claim 1, wherein the cationic lipid is DDAB.

8. The method of claim 1, wherein the cationic lipid is DMTAP.

9. The method of claim 1, wherein the oligonucleotide is 5'-GTGCTCCATT.GATGC-3' (SEQ ID NO: 1).

10. The method of claim 9, wherein said oligonucleotide comprises at least one modified base.

* * * * *